US008148100B2

(12) United States Patent
Schofield et al.

(10) Patent No.: US 8,148,100 B2
(45) Date of Patent: Apr. 3, 2012

(54) MINA53 ASSAYS

(75) Inventors: Christopher Joseph Schofield, Oxford (GB); Michael Arnold McDonough, Oxford (GB); Nicolas Joseph Jean Granatino, Oxford (GB)

(73) Assignee: ISIS Innovation Limited, Oxfordshire (GB)

( * ) Notice: Subject to any disclaimer, the term of this patent is extended or adjusted under 35 U.S.C. 154(b) by 804 days.

(21) Appl. No.: 12/088,144

(22) PCT Filed: Sep. 25, 2006

(86) PCT No.: PCT/GB2006/003547
§ 371 (c)(1),
(2), (4) Date: Oct. 8, 2008

(87) PCT Pub. No.: WO2007/034214
PCT Pub. Date: Mar. 29, 2007

(65) Prior Publication Data
US 2009/0208475 A1      Aug. 20, 2009

(30) Foreign Application Priority Data

Sep. 26, 2005   (GB) .................................. 0519605.0

(51) Int. Cl.
C12Q 1/26    (2006.01)
C12N 9/02    (2006.01)
C12N 1/20    (2006.01)
C12N 15/00   (2006.01)
C12P 21/04   (2006.01)
C07H 21/04   (2006.01)

(52) U.S. Cl. ........ 435/25; 435/189; 435/69.1; 435/71.1; 435/252.3; 435/320.1; 435/440; 536/23.2

(58) Field of Classification Search ........................ None
See application file for complete search history.

(56) References Cited

U.S. PATENT DOCUMENTS

| 5,916,898 | A | 6/1999 | Edwards et al. |
| 6,200,974 | B1 | 3/2001 | Edwards et al. |
| 2003/0153503 | A1 | 8/2003 | Klaus et al. |
| 2003/0176317 | A1 | 9/2003 | Guenzler-Pukall et al. |
| 2004/0053245 | A1* | 3/2004 | Tang et al. ........................ 435/6 |
| 2004/0053977 | A1 | 3/2004 | Almstead et al. |

FOREIGN PATENT DOCUMENTS

| DE | 3818850 A1 | 12/1989 |
| EP | 1500701 A1 | 1/2005 |
| WO | 02074981 A2 | 9/2002 |
| WO | 03042363 A2 | 5/2003 |
| WO | 03080566 A2 | 10/2003 |
| WO | 2004035812 A2 | 4/2004 |
| WO | 2004058252 A2 | 7/2004 |
| WO | 2005093411 A2 | 10/2005 |

OTHER PUBLICATIONS

Branden et al. Introduction to Protein Structure, Garland Publishing Inc., New York, p. 247, 1991.*
Bickel et al., "Selective Inhibition of Hepatic Collagen Accumulation in Experimental Liver Fibrosis in Rats by a New Prolyl 4-Hydroxylase Inhibitor", 1998, Hepatology, vol. 28, No. 2, p. 404-411.
Altschul et al., "Basic Local Alignment Search Tool", 1990, Journal of Molecular Biology, vol. 215, pp. 403-410.
Altschul, "A Protein Alignment Scoring System Sensitive at All Evolutionary Distances", 1993, Journal of Molecular Evolution, vol. 36, pp. 290-300.
Aoyagi et al., "Prolyl 4-Hydroxylase Inhibitor Is More Effective for the Inhibition of Proliferation Than for Inhibition of Collagen Synthesis of Rat Hepatic Stellate Cells", 2002, Hepatology Research, vol. 23, pp. 1-6.
Baader et al., "Inhibition of Prolyl 4-Hydroxylase by Oxalyl Amino Acid Derivatives in Vitro, in Isolated Microsomes and in Embryonic Chicken Tissues", 1994, Biochemical Journal, vol. 300, pp. 525-530.
Clissold et al, "JmjC: Cupin Metalloenzyme-Like Domains in Jumonji, Hairless and Phospholipase A2b", Jan. 2001, Trends in Biochemical Sciences, vol. 26, No. 1, pp. 7-9.
Cunliffe et al., "Inhibition of Prolyl 4-Hydroxylase by Hydroxyanthraquinones", 1986, Biochemical Journal, vol. 239, pp. 311-315.
Cunliffe et al., "Assay of Prolyl 4-Hydroxylase by the Chromatographic Determination of [14C]Succinic Acid on Ion-Exchange Minicolumns", 1986, Biochemical Journal, vol. 240, pp. 617-619.
Cunliffe et al., "Novel Inhibitors of Prolyl 4-Hydroxylase. 3. Inhibition by the Substrate Analogue N-Oxaloglycine and Its Derivatives", 1992, Journal of Medicinal Chemistry, vol. 35, pp. 2652-2658.
Devereux et al., "A Comprehensive Set of Sequence Analysis Programs for the VAX", 1984, Nucleic Acids Research, vol. 12, No. 1, pp. 387-395.
Dowell et al., "Novel Inhibitors of Prolyl 4-Hydroxylase. Part 4. Pyridine-2-Carboxylic Acid Analogues with Alternative 2-Substituents", 1993, European Journal of Medicinal Chemistry, vol. 28, pp. 513-516.
Dunwell et al., "Cupins: The Most Functionally Diverse Protein Superfamily?", 2004, Phytochemistry, vol. 65, pp. 7-17.
Eilbracht et al, "Protein NO52—A Constitutive Nucleolar Component Sharing High Sequence Homologies to Protein NO66", 2005, European Journal of Cell Biology, vol. 84, pp. 279-294.
Franklin et al., "Inhibition of Collagen Hydroxylation by 2,7,8-Trihydroxyanthraquinone in Embryonic-Chick Tendon Cells", 1989, Biochemical Journal, vol. 261, pp. 127-130.
Franklin, "Therapeutic Approaches to Organ Fibrosis", 1997, The International Journal of Biochemistry & Cell Biology, vol. 29, No. 1, pp. 79-89.
Franklin et al., "Inhibition of Prolyl 4-Hydroxylase In Vitro and In Vivo by Members of a Novel Series of Phenanthrolinones", 2001, Biochemical Journal, vol. 353, pp. 333-338.
Friedman et al., "Prolyl 4-Hydroxylase is Required for Viability and Morphogenesis in Caenorhabditis elegans", Apr. 25, 2000, PNAS, vol. 97, No. 9, pp. 4736-4741.
Gershkovich et al., "Fluorogenic Substrates for Proteases Based on Intramolecular Fluorescence Energy Transfer(IFETS)", 1996, Journal of Biochemical and Biophysical Methods, vol. 33, pp. 135-162.
Hausinger, "Fe(II)a-Ketoglutarate-Dependent Hydroxylases and Related Enzymes", 2004, Critical Reviews in Biochemistry and Molecular Biology, vol. 39, pp. 21-68.

(Continued)

Primary Examiner — Yong Pak
(74) Attorney, Agent, or Firm — Brooks Kushman P.C.

(57) ABSTRACT

The present invention comprises a method for assaying oxygenase activity the method comprising monitoring oxygenase activity of Mina53.

11 Claims, 2 Drawing Sheets

OTHER PUBLICATIONS

Higashide et al., "Alahopcin, A New Dipeptide Antibiotic Produced by *Streptomyces albulus* Subsp. *ochragerus* Subsp. Nov."., Mar. 1985, The Journal of Antibiotics, vol. XXXVIII, No. 3, pp. 285-295.

Ivan et al., "Biochemical Purification and Pharmacological Inhibition of a Mammalian Prolyl Hydroxylase Acting on Hypoxia-Inducible Factor", Oct. 15, 2002, PNAS, vol. 99, No. 21, pp. 13459-13464.

Krafft et al., "[6] Synthetic Approaches to Continuous Assays of Retroviral Proteases", 1994, Methods in Enzymology, vol. 241, pp. 70-86.

Lerner et al., "X-Ray Crystal Structure of a Bisubstrate Inhibitor Bound to the Enzyme Catechol-O-methyltransferase: A Dramatic Effect of Inhibitor Preorganization on Binding Affinity", 2001, Angewandte Chemie International Edition, vol. 40, No. 21, pp. 4040-4042.

McNeill et al., "A Fluorescence-Based Assay for 2-Oxoglutarate-Dependent Oxygenases", 2005, Analytical Biochemistry, vol. 336, pp. 125-131.

Mole et al., "2-Oxoglutarate Analogue Inhibitors of HIF Prolyl Hydroxylase", 2003, Bioorganic & Medicinal Chemistry Letters, vol. 13, pp. 2677-2680.

Muhling et al., "Quantitative Determination of Free Intracellular a-keto Acids in Neutrophils", 2003, Journal of Chromatography B, vol. 789, pp. 383-392.

Myllyla et al., "The Role of Ascorbate in the Prolyl Hydroxylase Reaction", Jul. 28, 1978, Biochemical and Biophysical Research Communications, vol. 83, No. 2, pp. 441-448.

Myllyharju et al., "Characterization of the Iron- and 2-Oxoglutarate-Binding Sites of Human Prolyl 4-Hydroxylase", 1997, The EMBO Journal, vol. 16, No. 6, pp. 1173-1180.

Myllyharju et al., "Collagens and Collagen-Related Diseases", 2001, Annals of Medicine, vol. 33, No. 1, pp. 7-21.

Nwogu et al., "Inhibition of Collagen Synthesis with Prolyl 4-Hydroxylase Inhibitor Improves Left Ventricular Function and Alters the Pattern of Left Ventricular Dilatation After Myocardial Infarction", Oct. 30, 2001, Circulation, vol. 104, No. 18, pp. 2216-2221.

Ohta et al, "The Absolute Configuration of P-1894B, A Potent Prolyl Hydroxylase Inhibitor", 1984, Chemical & Pharmaceutical Bulletin, vol. 32, No. 11, pp. 4350-4359.

Owicki, "Fluorescence Polarization and Anisotropy in High Throughput Screening: Perspectives and Primer", 2000, Journal of Biomolecular Screening, vol. 5, No. 5, pp. 297-306.

Pang et al., "Crystal Structure of Human Pirin. An Iron-Binding Nuclear Protein and Transcription Cofactor", Jan. 9, 2004, The Journal of Biological Chemistry, vol. 279, No. 2, pp. 1491-1498.

Ryle et al., "Non-Heme Iron Oxygenases", 2002, Current Opinions in Chemical Biology, vol. 6, pp. 193-201.

Sabourin et al., "Purification and Characterization of an a-Ketoisocaproate Oxygenase of Rat Liver", Jul. 10, 1982, The Journal of Biological Chemistry, vol. 257, pp. 7460-7467.

Schofield et al., "Mechanistic Studies on 2-Oxoglutarate Dependent Oxygenases", 1999, Journal of Inorganic Biochemistry, vol. 74, p. 49.

Teye et al., "Increased Expression of Myc Target Gene Mina53 in Human Colon Cancer", Jan. 2004, American Journal of Pathology, vol. 164, No. 1, pp. 205-216.

Tsuneoka et al., "A Novel Myc Target Gene, Mina53, That Is Involved in Cell Proliferation", Sep. 20, 2002, The Journal of Biological Chemistry, vol. 277, No. 38, pp. 35450-35459.

Tsuneoka et al., "Mina53 as a Potential Prognostic Factor for Esophageal Squamous Cell Carcinoma", Nov. 1, 2004, Clinical Cancer Research, vol. 10, pp. 7347-7356.

Wang et al., "Stuructures of *Aquifex aeolicus* KDO8P Synthase in Complex with R5P and PEP, and With a Bisubstrate Inhibitor: Role of Active Site Water in Catalysis", 2001, Biochemistry, vol. 40, pp. 15676-15683.

Wu et al., "Mechanism-Based Inactivation of the Human Prolyl-4-Hydroxylase by 5-Oxaproline-Containing Peptides: Evidence for a Prolyl radical Intermediate", 1999, Journal of the American Chemical Society, vol. 121, pp. 587-588.

Zhang et al., "Expression, Purification and Characterization of 1-Aminocyclopropance-1-Carboxylate Oxidase From Tomato in *Escherichia coli*", 1995, Biochemical Journal, vol. 307, pp. 77-85.

Zhang et al., "The Human Mineral Dust-Induced Gene, mdig, Is a Cell Growth Regulating Gene Associated with Lung Cancer", 2004, Oncogene, vol. 24, pp. 4873-4882.

Bickel et al., "Beneficial Effects of Inhibitors of Prolyl 4-Hydroxylase in CC14-Induced Fibrosis of the Liver in Rats", 1991, Journal of Hepatology vol. 13, Supp.3, p. S26-S34.

Masimirembwa et al., "In Vitro High Throughput Screening of Compounds for Favorable Metabolic Properties in Drug Discovery", 2001, Combinatorial Chemistry & High Throughput Screening vol. 4, No. 3, p. 245-263.

Baader et al., "Interference in Clinical Laboratory Tests, With Special Regard to the Bilirubin Assay: Effects of a Metabolite of the New Prolyl 4-Hydroxylase Inhibitor, Lufironil", 1994, Eur. J. Clin. Chem. Clin. Biochem. vol. 32, No. 7, p. 515-520.

* cited by examiner

```
1H2K
NO66     1   MDGLQASAGPLRRGRPRRRKPQPHSGSVLALPLRSRKIRKQLRSVVSRMAALRTQTLPS
Mina53   1   M...PKKAKPTGSGKEE..........................................
1H2K     1   M..................................................AATA......

1H2K                                              →  →    ΩΩΩ        →
NO66    61   ENSEESRVESTADDLGDALPGGAAVAAVPDAARREPYGHLGPAELLEASPAARSLQTPSA
Mina53  15   .......................................GPA................
1H2K     6   .........................AEAVASGSGEPREEAGALGPA.WDESQLRSYSFPTRPI 1H2K              →     ΩΩΩΩΩΩΩΩ        →
NO66   121   RLVPASAPPARLVEVPAAPVRVVETSALLCTAQHLAAVQSSGAPATASGPQVDNTGGEPA
Mina53  18   .........PCKQMKLEAA........................GGPSALN......
1H2K    43   PRLSQSDPRAEELIENEEPVVLTDTNLV............................

1H2K                                            ΩΩΩΩΩ  ΩΩΩΩΩΩΩ        -
NO66   181   WDSPLRRVLAELNRIPSSRRRAARLFEWLIAPMPPDHFYRRLWEREAVLVRRQDH...TY
Mina53  35   FDSP..............SSLFESLISPIKTETFFKEFWEQKPLLIQRDDPALATY
1H2K    71   ...................YPALKWDLEYLQENIGNG...DF 1H2K          →           →            ΩΩΩΩΩΩΩ       →    ΩΩΩΩΩΩΩΩΩΩΩΩ
NO66   238   YQGLFSTADLDSMLRNEEVQFGQHLDAARYINGRRETLNPPGRA..LPAAAWSLYQAGCS
Mina53  77   YGSLFKLTDLKSLC.SRGMYYGRDVNVCRCVNGKKKVLNKDGKAH.FLQLRKDFDQKRAT
1H2K    91   SVYSASTHKFL........YYDEKKMANFQNTKPRSNREEMKFHEFVEKLQDIQQRGGE 1H2K               →     TT  ΩΩΩΩΩΩΩ    ΩΩΩΩΩΩΩΩΩΩ     →           →   TT   →
NO66   296   LRLLCPDAFSTTV............YQFLAVLQEQFG.SMAGSNYLTPPNSQGFAPYD
Mina53 135   IQFHQPQRFKDEL............WRIQEKLECYFG.SLVGSNVYITPAGSQGLPPYD
1H2K   142   ERLYLQQTLNDTVGRKIVMDFLGFNMNWINKQQGKRCWGQLTSNLLLIGMEGNVTPAYD 1H2K           →           →       ΩΩΩΩΩΩΩ    TT          TT       ΩΩΩ.ΩΩ  -
NO66   343   DIEAFVLQLEGRKLWRVYRER............APTEELALTSS......PNFSQDDLG
Mina53 182   DVEVFILQLEGKHWRLYHPT............VPLAREYSVE.........ABERIC
1H2K   202   EQQNFFAQIKCYKRCILFPPDQFECLYPYPVHHPCDRQSQVDFDNPDYERFPNF.QNVVC
```

Figure 1A

```
1H2K         ...――→   TT ――→   TT ――→           TT      ――――――――  ............
NO66    384  EPVLQTVLEPGDLLYFPRGFIHQAECQDGV.HSLHLTLSYYQRNTMGDFLEAILPLAVQA
Mina53  219  RPVHEFMLKPGDLLYFPRGTIHQADTPAGLAHSTHVTISYYQNNSWGDFLLDTISGLVFD
1H2K    261  ...YETVVGPCDVLYIPMYWWHHTES......LLNGGIIIIDVNFW..............

1H2K         ................――→          ΩΩΩΩΩΩΩΩΩΩΩΩΩΩΩΩΩΩ....
NO66    443  AMEENVEFRRGLPRDFMDYMGAQHSDSKDPRRTAFMEKVRVLVARLGHFAPVDAVADQRA
Mina53  279  TAKEDVELRTGIPRQLL..LQVESTTVATRRLSGFL...RTLADRLE..GTKELLSSDMK
1H2K    297  ................YKGAP.....TPKRIEYPLKAHQKVAIMRNIEKMLGEA....

1H2K         ..........................Ω   ΩΩΩΩΩΩΩΩΩ..............
NO66    503  KDFIHDSLPPVLTDRERALSVYGLPIRWEAGEPVNMGAQLTTETEVHMLQDGIARLVGEG
Mina53  332  KDFIMHRLPPYSAGDGAELSTPGGKLPRLDSV...VRLQFKDHIVLTVLPDQDQSDETQE
1H2K    330  ..........................LGNPQEMGPLLNT................

1H2K         .........................................ΩΩ
NO66    563  GHLFLYYTVENSRVYHL......EEPKCLEIYPQQADAMELILGSYPEFVRVGDLPCDSV
Mina53  389  KMVYIYHSLKNSRETHMMGNEEETEFHGLRFPLSHLDALKQIWNS..PAISVKDLKLTTD
1H2K    343  .........................................MIKGRY..............

1H2K
NO66    617  EDQLSLATTLYDKGLLLTKMPLALN
Mina53  447  EEKESLVLSLWTECLIQVV......
1H2K    349  .........................N
```

Figure 1B

SEQUENCE LISTING

<160> NUMBER OF SEQ ID NOS: 4

<210> SEQ ID NO 1
<211> LENGTH: 2048
<212> TYPE: DNA
<213> ORGANISM: Homo sapiens
<220> FEATURE:
<221> NAME/KEY: CDS
<222> LOCATION: (265)..(1662)

<400> SEQUENCE: 1

```
gcggaagcct tggttacaga gagtcgcaca cgtggcctgc taatggtcgc gacaccggtg      60
acgagcgcac ggaaagtttg gaggcttagc aaggagggtg gtgccggcct ccgcccggtg     120
gtggcagaac tgcctgtgcg agcacggctt ccacgtgggc tgcgccgccg gcgtcatgt     180 cgggcctaag agacacgctc tacagctgtg aaatctgaag ttcaggtttg catttcctta     240
ctgctttgtc ttgaagacag aacg atg cca aag aaa gca aag cct aca ggg       291
                            Met Pro Lys Lys Ala Lys Pro Thr Gly
                            1               5 agt ggg aag gaa gag ggg ccg gct ccc tgt aag cag atg aag tta gaa       339
Ser Gly Lys Glu Glu Gly Pro Ala Pro Cys Lys Gln Met Lys Leu Glu
 10              15                  20                  25 gca gct ggg ggg cct tca gct tta aac ttt gac agt ccc agt agt ctc       387
Ala Ala Gly Gly Pro Ser Ala Leu Asn Phe Asp Ser Pro Ser Ser Leu
                 30                  35                  40 ttt gaa agt tta atc tcg ccc atc aag aca gag act ttt ttc aag gaa       435
Phe Glu Ser Leu Ile Ser Pro Ile Lys Thr Glu Thr Phe Phe Lys Glu
             45                  50                  55 ttc tgg gag cag aag ccc ctt ctc att cag aga gat gac cct gca ctg       483
Phe Trp Glu Gln Lys Pro Leu Leu Ile Gln Arg Asp Asp Pro Ala Leu
         60                  65                  70 gcc aca tac tat ggg tcc ctg ttc aag cta aca gat ctg aag agt ctg       531
Ala Thr Tyr Tyr Gly Ser Leu Phe Lys Leu Thr Asp Leu Lys Ser Leu
 75                  80                  85 tgc agc cgg ggg atg tac tat gga aga gat gtg aat gtc tgc cgg tgt       579
Cys Ser Arg Gly Met Tyr Tyr Gly Arg Asp Val Asn Val Cys Arg Cys
 90                  95                 100                 105 gtc aat ggg aag aag aag gtt tta aat aaa gat ggc aaa gca cac ttt       627
Val Asn Gly Lys Lys Lys Val Leu Asn Lys Asp Gly Lys Ala His Phe
                110                 115                 120 ctt cag ctg aga aaa gat ttt gat cag aaa agg gca acg att cag ttt       675
Leu Gln Leu Arg Lys Asp Phe Asp Gln Lys Arg Ala Thr Ile Gln Phe
            125                 130                 135 cac caa cct cag aga ttt aag gat gag ctt tgg agg atc cag gag aag       723
His Gln Pro Gln Arg Phe Lys Asp Glu Leu Trp Arg Ile Gln Glu Lys
        140                 145                 150 ctg gaa tgt tac ttt ggc tcc ttg gtt ggc tcg aat gtg tac ata act       771
Leu Glu Cys Tyr Phe Gly Ser Leu Val Gly Ser Asn Val Tyr Ile Thr
155                 160                 165 ccc gca gga tct cag ggc ctg ccg ccc cat tat gat gat gtc gag gtt       819
Pro Ala Gly Ser Gln Gly Leu Pro Pro His Tyr Asp Asp Val Glu Val
170                 175                 180                 185 ttc atc ctg cag ctg gag gga gag aaa cac tgg cgc ctc tac cac ccc       867
Phe Ile Leu Gln Leu Glu Gly Glu Lys His Trp Arg Leu Tyr His Pro
                190                 195                 200 act gtg ccc ctg gca cga gag tac agc gtg gag gcc gag gaa agg atc       915
Thr Val Pro Leu Ala Arg Glu Tyr Ser Val Glu Ala Glu Glu Arg Ile
            205                 210                 215 ggc agg ccg gtg cat gag ttt atg ctg aag ccg ggt gat ttg ttg tac       963
Gly Arg Pro Val His Glu Phe Met Leu Lys Pro Gly Asp Leu Leu Tyr
        220                 225                 230 ttt ccc aga gga acc att cat caa gcg gac act cct gcg ggg ctg gcc      1011
Phe Pro Arg Gly Thr Ile His Gln Ala Asp Thr Pro Ala Gly Leu Ala
235                 240                 245 cac tcg act cac gtg acc atc agc acc tac cag aac aat tca tgg gga      1059
His Ser Thr His Val Thr Ile Ser Thr Tyr Gln Asn Asn Ser Trp Gly
250                 255                 260                 265 gat ttc ctt ttg gat acc atc tcg ggg ctt gta ttt gat act gca aag      1107
Asp Phe Leu Leu Asp Thr Ile Ser Gly Leu Val Phe Asp Thr Ala Lys
                270                 275                 280
```

```
gaa gac gtg gag tta cgg acc ggc ata ccc cgg cag ctg ctc ctg cag    1155
Glu Asp Val Glu Leu Arg Thr Gly Ile Pro Arg Gln Leu Leu Leu Gln
            285                 290                 295 gtg gaa tcc aca act gtt gct aca aga cga tta agt ggc ttc ctg agg    1203
Val Glu Ser Thr Thr Val Ala Thr Arg Arg Leu Ser Gly Phe Leu Arg
    300                 305                 310 aca ctt gca gac cgg ctg gag ggc acc aaa gaa ctg ctt tcc tca gac    1251
Thr Leu Ala Asp Arg Leu Glu Gly Thr Lys Glu Leu Leu Ser Ser Asp
315                 320                 325 atg aag aag gat ttt att atg cac aga ctc ccc cct tac tct gcg gga    1299
Met Lys Lys Asp Phe Ile Met His Arg Leu Pro Pro Tyr Ser Ala Gly
330                 335                 340                 345 gat ggg gca gag ctg tca aca cca ggt gga aag tta ccg agg ctg gac    1347
Asp Gly Ala Glu Leu Ser Thr Pro Gly Gly Lys Leu Pro Arg Leu Asp
                350                 355                 360 agt gta gtg aga ctg cag ttt aaa gac cac att gtc ctc aca gta ctg    1395
Ser Val Val Arg Leu Gln Phe Lys Asp His Ile Val Leu Thr Val Leu
            365                 370                 375 ccg gat caa gat caa tct gat gaa act caa gaa aag atg gtg tac atc    1443
Pro Asp Gln Asp Gln Ser Asp Glu Thr Gln Glu Lys Met Val Tyr Ile
        380                 385                 390 tat cat tcc tta aag aat agt aga gag aca cac atg atg gga aat gag    1491
Tyr His Ser Leu Lys Asn Ser Arg Glu Thr His Met Met Gly Asn Glu
    395                 400                 405 gag gaa aca gag ttt cat gga ctt cgc ttc cct ttg tca cat ttg gat    1539
Glu Glu Thr Glu Phe His Gly Leu Arg Phe Pro Leu Ser His Leu Asp
410                 415                 420                 425 gca ctg aag caa att tgg aat agt cca gct att tct gtc aag gac ctg    1587
Ala Leu Lys Gln Ile Trp Asn Ser Pro Ala Ile Ser Val Lys Asp Leu
                430                 435                 440 aaa ctt act aca gat gag gaa aag gaa agc ctg gta tta tcc ctc tgg    1635
Lys Leu Thr Thr Asp Glu Glu Lys Glu Ser Leu Val Leu Ser Leu Trp
            445                 450                 455 aca gaa tgt tta att caa gta gtc tag tgcctttgca gaatcaaatg          1682
Thr Glu Cys Leu Ile Gln Val Val
        460                 465 cctactattt tatatgcata tattaaaaga aaagcaaaga cctgagccga ggagaggatg   1742
aattcaagtt tccttacctg cgtatctact acaaacatg agacctccct gttacaggtg    1802
gtcagttggc aaatgtact aacgggcaca tgaaagaaag aacagcaaat taccaagtgt    1862
ctcagaaaat gacaaaacca tattttgaca agtttattta atccagtgtg gtagaaaagg   1922
cacaattcca atgtatcatt tagaattgaa tgtcattaac ctggctttgt tctttggaag   1982
aaacaacttc tttaaagagc ttctttggct ctagaaaaat ttcaaacaat taaaaaaaaa   2042
aaaaaa                                                              2048

<210> SEQ ID NO 2
<211> LENGTH: 465
<212> TYPE: PRT
<213> ORGANISM: Homo sapiens
<220> FEATURE:

<400> SEQUENCE: 2

Met Pro Lys Lys Ala Lys Pro Thr Gly Ser Gly Lys Glu Glu Gly Pro
1               5                   10                  15

Ala Pro Cys Lys Gln Met Lys Leu Glu Ala Ala Gly Gly Pro Ser Ala
            20                  25                  30

Leu Asn Phe Asp Ser Pro Ser Ser Leu Phe Glu Ser Leu Ile Ser Pro
        35                  40                  45
```

-continued

```
Ile Lys Thr Glu Thr Phe Phe Lys Glu Phe Trp Glu Gln Lys Pro Leu
         50                  55                  60
Leu Ile Gln Arg Asp Asp Pro Ala Leu Ala Thr Tyr Tyr Gly Ser Leu
 65                  70                  75                  80
Phe Lys Leu Thr Asp Leu Lys Ser Leu Cys Ser Arg Gly Met Tyr Tyr
                 85                  90                  95
Gly Arg Asp Val Asn Val Cys Arg Cys Val Asn Gly Lys Lys Lys Val
             100                 105                 110
Leu Asn Lys Asp Gly Lys Ala His Phe Leu Gln Leu Arg Lys Asp Phe
         115                 120                 125
Asp Gln Lys Arg Ala Thr Ile Gln Phe His Gln Pro Gln Arg Phe Lys
130                 135                 140
Asp Glu Leu Trp Arg Ile Gln Glu Lys Leu Glu Cys Tyr Phe Gly Ser
145                 150                 155                 160
Leu Val Gly Ser Asn Val Tyr Ile Thr Pro Ala Gly Ser Gln Gly Leu
                 165                 170                 175
Pro Pro His Tyr Asp Asp Val Glu Val Phe Ile Leu Gln Leu Glu Gly
             180                 185                 190
Glu Lys His Trp Arg Leu Tyr His Pro Thr Val Pro Leu Ala Arg Glu
         195                 200                 205
Tyr Ser Val Glu Ala Glu Arg Ile Gly Arg Pro Val His Glu Phe
210                 215                 220
Met Leu Lys Pro Gly Asp Leu Leu Tyr Phe Pro Arg Gly Thr Ile His
225                 230                 235                 240
Gln Ala Asp Thr Pro Ala Gly Leu Ala His Ser Thr His Val Thr Ile
                 245                 250                 255
Ser Thr Tyr Gln Asn Asn Ser Trp Gly Asp Phe Leu Leu Asp Thr Ile
             260                 265                 270
Ser Gly Leu Val Phe Asp Thr Ala Lys Glu Asp Val Glu Leu Arg Thr
         275                 280                 285
Gly Ile Pro Arg Gln Leu Leu Leu Gln Val Glu Ser Thr Thr Val Ala
290                 295                 300
Thr Arg Arg Leu Ser Gly Phe Leu Arg Thr Leu Ala Asp Arg Leu Glu
305                 310                 315                 320
Gly Thr Lys Glu Leu Leu Ser Ser Asp Met Lys Lys Asp Phe Ile Met
                 325                 330                 335
His Arg Leu Pro Pro Tyr Ser Ala Gly Asp Gly Ala Glu Leu Ser Thr
             340                 345                 350
Pro Gly Gly Lys Leu Pro Arg Leu Asp Ser Val Val Arg Leu Gln Phe
         355                 360                 365
Lys Asp His Ile Val Leu Thr Val Leu Pro Asp Gln Asp Gln Ser Asp
370                 375                 380
Glu Thr Gln Glu Lys Met Val Tyr Ile Tyr His Ser Leu Lys Asn Ser
385                 390                 395                 400
Arg Glu Thr His Met Met Gly Asn Glu Glu Thr Glu Phe His Gly
                 405                 410                 415
Leu Arg Phe Pro Leu Ser His Leu Asp Ala Leu Lys Gln Ile Trp Asn
             420                 425                 430
Ser Pro Ala Ile Ser Val Lys Asp Leu Lys Leu Thr Thr Asp Glu Glu
         435                 440                 445
Lys Glu Ser Leu Val Leu Ser Leu Trp Thr Glu Cys Leu Ile Gln Val
450                 455                 460
Val
```

465

```
<210> SEQ ID NO 3
<211> LENGTH: 1926
<212> TYPE: DNA
<213> ORGANISM: Homo sapiens
<220> FEATURE:
<221> NAME/KEY: CDS
<222> LOCATION: (1)..(1926)

<400> SEQUENCE: 3
```

| | | | | | | | | | | | | | | | | |
|---|---|---|---|---|---|---|---|---|---|---|---|---|---|---|---|---|
| atg | gat | ggg | ctc | cag | gcc | agt | gca | ggg | ccg | ttg | agg | cgc | ggg | cgg | ccg | 48 |
| Met | Asp | Gly | Leu | Gln | Ala | Ser | Ala | Gly | Pro | Leu | Arg | Arg | Gly | Arg | Pro | |
| 1 | | | | 5 | | | | | 10 | | | | | 15 | | |
| agg | cgc | cgg | cgc | aag | ccc | cag | cca | cac | agc | ggg | tcg | gtc | ctg | gcc | ctg | 96 |
| Arg | Arg | Arg | Arg | Lys | Pro | Gln | Pro | His | Ser | Gly | Ser | Val | Leu | Ala | Leu | |
| | | | 20 | | | | | 25 | | | | | 30 | | | |
| ccc | ttg | agg | tcc | agg | aag | ata | cga | aag | cag | ctg | cga | agt | gtt | gta | tcc | 144 |
| Pro | Leu | Arg | Ser | Arg | Lys | Ile | Arg | Lys | Gln | Leu | Arg | Ser | Val | Val | Ser | |
| | | 35 | | | | | 40 | | | | | 45 | | | | |
| cgc | atg | gca | gcg | ctg | agg | acg | cag | acg | ctg | cct | agc | gag | aac | tcg | gag | 192 |
| Arg | Met | Ala | Ala | Leu | Arg | Thr | Gln | Thr | Leu | Pro | Ser | Glu | Asn | Ser | Glu | |
| | 50 | | | | | 55 | | | | | 60 | | | | | |
| gaa | tcg | agg | gtg | gag | tcg | acg | gcc | gac | gac | ctg | ggg | gac | gcg | cta | ccc | 240 |
| Glu | Ser | Arg | Val | Glu | Ser | Thr | Ala | Asp | Asp | Leu | Gly | Asp | Ala | Leu | Pro | |
| 65 | | | | | 70 | | | | | 75 | | | | | 80 | |
| ggt | ggg | gcg | gcg | gtg | gcg | gcc | gtc | ccg | gac | gca | gcc | cgg | cga | gag | cca | 288 |
| Gly | Gly | Ala | Ala | Val | Ala | Ala | Val | Pro | Asp | Ala | Ala | Arg | Arg | Glu | Pro | |
| | | | | 85 | | | | | 90 | | | | | 95 | | |
| tac | ggc | cac | ctg | ggg | ccc | gca | gag | ctg | ctg | gag | gcc | tcg | ccc | gcc | gcg | 336 |
| Tyr | Gly | His | Leu | Gly | Pro | Ala | Glu | Leu | Leu | Glu | Ala | Ser | Pro | Ala | Ala | |
| | | | | 100 | | | | | 105 | | | | | 110 | | |
| cgc | tcc | ctg | cag | acc | ccg | tcg | gcg | cgc | ctg | gtg | ccc | gct | tcc | gcg | ccg | 384 |
| Arg | Ser | Leu | Gln | Thr | Pro | Ser | Ala | Arg | Leu | Val | Pro | Ala | Ser | Ala | Pro | |
| | | | 115 | | | | | 120 | | | | | 125 | | | |
| ccc | gcg | cgc | ctg | gtg | gag | gtg | ccc | gcc | gcg | ccg | gtc | cgg | gtg | gtg | gag | 432 |
| Pro | Ala | Arg | Leu | Val | Glu | Val | Pro | Ala | Ala | Pro | Val | Arg | Val | Val | Glu | |
| | | 130 | | | | | 135 | | | | | 140 | | | | |
| acc | tcg | gcc | ctg | ctg | tgc | acc | gcg | caa | cac | tta | gcg | gcc | gtc | cag | tcg | 480 |
| Thr | Ser | Ala | Leu | Leu | Cys | Thr | Ala | Gln | His | Leu | Ala | Ala | Val | Gln | Ser | |
| 145 | | | | | 150 | | | | | 155 | | | | | 160 | |
| tcc | ggg | gcc | cct | gcg | acg | gcg | tcg | ggg | ccg | cag | gtg | gat | aac | acg | ggt | 528 |
| Ser | Gly | Ala | Pro | Ala | Thr | Ala | Ser | Gly | Pro | Gln | Val | Asp | Asn | Thr | Gly | |
| | | | | 165 | | | | | 170 | | | | | 175 | | |
| ggg | gag | ccg | gcc | tgg | gac | tcc | ccg | cgg | cgc | gtc | ttg | gcc | gag | ctg | | 576 |
| Gly | Glu | Pro | Ala | Trp | Asp | Ser | Pro | Leu | Arg | Arg | Val | Leu | Ala | Glu | Leu | |
| | | | | 180 | | | | | 185 | | | | | 190 | | |
| aac | cgc | atc | ccc | agc | agc | cgg | cgg | cga | gcg | gcc | cgc | ctc | ttt | gag | tgg | 624 |
| Asn | Arg | Ile | Pro | Ser | Ser | Arg | Arg | Arg | Ala | Ala | Arg | Leu | Phe | Glu | Trp | |
| | | | 195 | | | | | 200 | | | | | 205 | | | |
| ctc | atc | gcg | ccc | atg | ccg | cca | gat | cac | ttc | tac | cgg | cgc | cta | tgg | gag | 672 |
| Leu | Ile | Ala | Pro | Met | Pro | Pro | Asp | His | Phe | Tyr | Arg | Arg | Leu | Trp | Glu | |
| | 210 | | | | | 215 | | | | | 220 | | | | | |
| cgc | gag | gcg | gtg | ctg | gtg | cgg | cgg | cag | gac | cac | acc | tac | tac | cag | gga | 720 |
| Arg | Glu | Ala | Val | Leu | Val | Arg | Arg | Gln | Asp | His | Thr | Tyr | Tyr | Gln | Gly | |
| 225 | | | | | 230 | | | | | 235 | | | | | 240 | |
| ctt | ttc | tct | acc | gct | gac | ctg | gat | tcg | atg | ctg | cgc | aac | gag | gag | gtg | 768 |
| Leu | Phe | Ser | Thr | Ala | Asp | Leu | Asp | Ser | Met | Leu | Arg | Asn | Glu | Glu | Val | |
| | | | | 245 | | | | | 250 | | | | | 255 | | |
| cag | ttc | ggc | cag | cat | ttg | gac | gcc | gct | cgc | tac | atc | aac | gga | cga | cgc | 816 |
| Gln | Phe | Gly | Gln | His | Leu | Asp | Ala | Ala | Arg | Tyr | Ile | Asn | Gly | Arg | Arg | |
| | | | | 260 | | | | | 265 | | | | | 270 | | |

|  |  |
|---|---|
| gag acc ctg aac cca ccc ggc cgc gcg ctg ccc gcc gcc gcg tgg tcc<br>Glu Thr Leu Asn Pro Pro Gly Arg Ala Leu Pro Ala Ala Ala Trp Ser<br>    275                            280                        285 | 864 |
| ctg tac cag gcc ggc tgc tcc ctg cgt ctc ctc tgt ccg cag gct ttc<br>Leu Tyr Gln Ala Gly Cys Ser Leu Arg Leu Leu Cys Pro Gln Ala Phe<br>    290                            295                        300 | 912 |
| tct act act gtg tgg cag ttt ttg gct gtg ctt caa gag cag ttt gga<br>Ser Thr Thr Val Trp Gln Phe Leu Ala Val Leu Gln Glu Gln Phe Gly<br>305                        310                        315                        320 | 960 |
| agc atg gca ggc tcc aac gtt tac ctc acg ccc cct aac tcg cag ggc<br>Ser Met Ala Gly Ser Asn Val Tyr Leu Thr Pro Pro Asn Ser Gln Gly<br>                          325                        330                        335 | 1008 |
| ttt gcc ccc cac tac gac gac atc gag gcc ttc gtg ctg cag ctg gaa<br>Phe Ala Pro His Tyr Asp Asp Ile Glu Ala Phe Val Leu Gln Leu Glu<br>                      340                        345                        350 | 1056 |
| ggt agg aaa ctc tgg cgt gta tac cga ccc cga gcc cca acc gag gaa<br>Gly Arg Lys Leu Trp Arg Val Tyr Arg Pro Arg Ala Pro Thr Glu Glu<br>            355                            360                        365 | 1104 |
| ctg gct ctg aca tcc agc ccc aac ttc agt cag gac gac ctc ggt gag<br>Leu Ala Leu Thr Ser Ser Pro Asn Phe Ser Gln Asp Asp Leu Gly Glu<br>370                        375                        380 | 1152 |
| ccg gtg ctg cag acc gtg ctg gaa cct gga gat ttg ctg tat ttt cct<br>Pro Val Leu Gln Thr Val Leu Glu Pro Gly Asp Leu Leu Tyr Phe Pro<br>385                        390                        395                        400 | 1200 |
| cgg ggc ttc att cac caa gct gaa tgc cag gat gga gtc cac tct ctg<br>Arg Gly Phe Ile His Gln Ala Glu Cys Gln Asp Gly Val His Ser Leu<br>                      405                        410                        415 | 1248 |
| cac ctc acc ttg tcc acg tac cag cgc aat acc tgg ggt gac ttc tta<br>His Leu Thr Leu Ser Thr Tyr Gln Arg Asn Thr Trp Gly Asp Phe Leu<br>                    420                        425                        430 | 1296 |
| gag gcc ata ctg cct ctg gca gtg cag gct gca atg gaa gaa aat gtg<br>Glu Ala Ile Leu Pro Leu Ala Val Gln Ala Ala Met Glu Glu Asn Val<br>                435                        440                        445 | 1344 |
| gag ttt cgg agg ggt ctg ccc cga gac ttc atg gat tac atg ggg gcc<br>Glu Phe Arg Arg Gly Leu Pro Arg Asp Phe Met Asp Tyr Met Gly Ala<br>450                        455                        460 | 1392 |
| cag cat tca gat tct aag gat ccg cga aga acc gct ttc atg gag aag<br>Gln His Ser Asp Ser Lys Asp Pro Arg Arg Thr Ala Phe Met Glu Lys<br>465                        470                        475                        480 | 1440 |
| gtg cgg gtc ttg gtt gcc cgc ctg gga cac ttt gct cct gtt gat gct<br>Val Arg Val Leu Val Ala Arg Leu Gly His Phe Ala Pro Val Asp Ala<br>                          485                        490                        495 | 1488 |
| gtg gcc gac cag cga gcc aaa gac ttc att cac gat tct ctg ccc cct<br>Val Ala Asp Gln Arg Ala Lys Asp Phe Ile His Asp Ser Leu Pro Pro<br>                  500                        505                        510 | 1536 |
| gtt ttg act gat agg gag agg gca cta agt gtt tac ggg ctt cca att<br>Val Leu Thr Asp Arg Glu Arg Ala Leu Ser Val Tyr Gly Leu Pro Ile<br>              515                        520                        525 | 1584 |
| cgc tgg gag gct gga gaa cct gta aac gtg ggg gcc cag ttg aca aca<br>Arg Trp Glu Ala Gly Glu Pro Val Asn Val Gly Ala Gln Leu Thr Thr<br>530                        535                        540 | 1632 |
| gaa aca gaa gtc cat atg ctt cag gat ggg ata gct cgg ctg gtg ggt<br>Glu Thr Glu Val His Met Leu Gln Asp Gly Ile Ala Arg Leu Val Gly<br>545                        550                        555                        560 | 1680 |
| gag ggg ggc cat ttg ttt ctc tat tac aca gtg gaa aac tcc cgt gtg<br>Glu Gly Gly His Leu Phe Leu Tyr Tyr Thr Val Glu Asn Ser Arg Val<br>                        565                        570                        575 | 1728 |
| tat cat ctg gaa gaa ccc aag tgc ttg gaa ata tac ccc cag caa gct<br>Tyr His Leu Glu Glu Pro Lys Cys Leu Glu Ile Tyr Pro Gln Gln Ala<br>                  580                        585                        590 | 1776 |

```
gat gcc atg gaa ctg ttg ctt ggt tct tat cca gag ttt gtg aga gtg      1824
Asp Ala Met Glu Leu Leu Leu Gly Ser Tyr Pro Glu Phe Val Arg Val
            595                 600                 605 ggg gac ctg ccc tgt gac agt gtg gag gac cag ctg tcc ttg gca acc      1872
Gly Asp Leu Pro Cys Asp Ser Val Glu Asp Gln Leu Ser Leu Ala Thr
        610                 615                 620 acg ttg tat gat aag ggg ctg ctg ctc act aag atg cct cta gcc cta      1920
Thr Leu Tyr Asp Lys Gly Leu Leu Leu Thr Lys Met Pro Leu Ala Leu
625                 630                 635                 640 aat tag                                                              1926
Asn

<210> SEQ ID NO 4
<211> LENGTH: 641
<212> TYPE: PRT
<213> ORGANISM: Homo sapiens
<220> FEATURE:

<400> SEQUENCE: 4

Met Asp Gly Leu Gln Ala Ser Ala Gly Pro Leu Arg Arg Gly Arg Pro
1               5                   10                  15

Arg Arg Arg Arg Lys Pro Gln Pro His Ser Gly Ser Val Leu Ala Leu
            20                  25                  30

Pro Leu Arg Ser Arg Lys Ile Arg Lys Gln Leu Arg Ser Val Val Ser
        35                  40                  45

Arg Met Ala Ala Leu Arg Thr Gln Thr Leu Pro Ser Glu Asn Ser Glu
    50                  55                  60

Glu Ser Arg Val Glu Ser Thr Ala Asp Asp Leu Gly Asp Ala Leu Pro
65                  70                  75                  80

Gly Gly Ala Ala Val Ala Ala Val Pro Asp Ala Ala Arg Arg Glu Pro
                85                  90                  95

Tyr Gly His Leu Gly Pro Ala Glu Leu Leu Glu Ala Ser Pro Ala Ala
            100                 105                 110

Arg Ser Leu Gln Thr Pro Ser Ala Arg Leu Val Pro Ala Ser Ala Pro
        115                 120                 125

Pro Ala Arg Leu Val Glu Val Pro Ala Ala Pro Val Arg Val Val Glu
    130                 135                 140

Thr Ser Ala Leu Leu Cys Thr Gln His Leu Ala Ala Val Gln Ser
145                 150                 155                 160

Ser Gly Ala Pro Ala Thr Ala Ser Gly Pro Gln Val Asp Asn Thr Gly
                165                 170                 175

Gly Glu Pro Ala Trp Asp Ser Pro Leu Arg Arg Val Leu Ala Glu Leu
            180                 185                 190

Asn Arg Ile Pro Ser Ser Arg Arg Arg Ala Ala Arg Leu Phe Glu Trp
        195                 200                 205

Leu Ile Ala Pro Met Pro Pro Asp His Phe Tyr Arg Arg Leu Trp Glu
    210                 215                 220

Arg Glu Ala Val Leu Val Arg Arg Gln Asp His Thr Tyr Tyr Gln Gly
225                 230                 235                 240

Leu Phe Ser Thr Ala Asp Leu Asp Ser Met Leu Arg Asn Glu Glu Val
                245                 250                 255

Gln Phe Gly Gln His Leu Asp Ala Ala Arg Tyr Ile Asn Gly Arg Arg
            260                 265                 270

Glu Thr Leu Asn Pro Pro Gly Arg Ala Leu Pro Ala Ala Ala Trp Ser
        275                 280                 285

Leu Tyr Gln Ala Gly Cys Ser Leu Arg Leu Leu Cys Pro Gln Ala Phe
```

-continued

```
                    290                 295                 300
Ser Thr Thr Val Trp Gln Phe Leu Ala Val Leu Gln Glu Gln Phe Gly
305                 310                 315                 320

Ser Met Ala Gly Ser Asn Val Tyr Leu Thr Pro Pro Asn Ser Gln Gly
                325                 330                 335

Phe Ala Pro His Tyr Asp Asp Ile Glu Ala Phe Val Leu Gln Leu Glu
                340                 345                 350

Gly Arg Lys Leu Trp Arg Val Tyr Arg Pro Arg Ala Pro Thr Glu Glu
            355                 360                 365

Leu Ala Leu Thr Ser Ser Pro Asn Phe Ser Gln Asp Asp Leu Gly Glu
            370                 375                 380

Pro Val Leu Gln Thr Val Leu Glu Pro Gly Asp Leu Leu Tyr Phe Pro
385                 390                 395                 400

Arg Gly Phe Ile His Gln Ala Glu Cys Gln Asp Gly Val His Ser Leu
                405                 410                 415

His Leu Thr Leu Ser Thr Tyr Gln Arg Asn Thr Trp Gly Asp Phe Leu
                420                 425                 430

Glu Ala Ile Leu Pro Leu Ala Val Gln Ala Ala Met Glu Glu Asn Val
            435                 440                 445

Glu Phe Arg Arg Gly Leu Pro Arg Asp Phe Met Asp Tyr Met Gly Ala
450                 455                 460

Gln His Ser Asp Ser Lys Asp Pro Arg Arg Thr Ala Phe Met Glu Lys
465                 470                 475                 480

Val Arg Val Leu Val Ala Arg Leu Gly His Phe Ala Pro Val Asp Ala
                485                 490                 495

Val Ala Asp Gln Arg Ala Lys Asp Phe Ile His Asp Ser Leu Pro Pro
                500                 505                 510

Val Leu Thr Asp Arg Glu Arg Ala Leu Ser Val Tyr Gly Leu Pro Ile
            515                 520                 525

Arg Trp Glu Ala Gly Glu Pro Val Asn Val Gly Ala Gln Leu Thr Thr
            530                 535                 540

Glu Thr Glu Val His Met Leu Gln Asp Gly Ile Ala Arg Leu Val Gly
545                 550                 555                 560

Glu Gly His Leu Phe Leu Tyr Tyr Thr Val Glu Asn Ser Arg Val
                565                 570                 575

Tyr His Leu Glu Glu Pro Lys Cys Leu Glu Ile Tyr Pro Gln Gln Ala
            580                 585                 590

Asp Ala Met Glu Leu Leu Leu Gly Ser Tyr Pro Glu Phe Val Arg Val
            595                 600                 605

Gly Asp Leu Pro Cys Asp Ser Val Glu Asp Gln Leu Ser Leu Ala Thr
            610                 615                 620

Thr Leu Tyr Asp Lys Gly Leu Leu Leu Thr Lys Met Pro Leu Ala Leu
625                 630                 635                 640

Asn
```

MINA53 ASSAYS

SEQUENCE LISTING

The text file is ISII0105PUSA.txt, created Apr. 8, 2009, and of size 25.9 KB, filed therewith, is hereby incorporated by reference.

FIELD OF THE INVENTION

The present invention relates to a 2-oxoglutarate (2-OG) oxygenase, and in particular, to assays using the purified 2-OG oxygenase to identify inhibitors and substrates. Inhibitors of the 2-OG oxygenase are useful in inhibiting cell proliferation and in treating cancer.

BACKGROUND TO THE INVENTION

MYC induced nuclear antigen, isoform 2 (Mina53) has been shown to be a target gene of c-Myc, suggesting that it is involved in mammalian cell proliferation (Tsuneoka et al. (2002) J. Biol. Chem. 277, 35450-9). Colon tumour cell lines were subsequently shown to highly express Mina53. Suppression of Mina53 expression severely suppressed proliferation of colon tumour cells in vitro and suppression of Mina53 or its activity may reduce cell proliferation and so be of use in the treatment of cancer. Elevated expression of Mina53 was therefore deemed a characteristic feature in colon cancer (Teye et al. (2004) Am. J. Pathol. 164, 205-16).

Reduction of Mina53 expression using RNAi has been shown to suppress cell proliferation in oesophageal squamous cell carcinoma (ESCC). Expression of Mina53 was also shown to be elevated in 83% of ESCC cell lines tested and patients with high expression level of Mina53 had shorter survival periods. Together, these results identify Mina53 as a potential prognostic factor for ESCC and indicate that inhibition of the unidentified role of Mina53 will be of benefit in treating cancer (Tsuneoka et al. (2004) Clin. Cancer Res. 10, 7347-56).

Mina53 was shown through immunoprecipitation to be part of a ribonucleoprotein complex where it associates with ribosomal as well as non-ribosomal proteins. It was proposed that Mina53 is involved in rRNA processing and/or ribosome assembly (Eilbract et al. (2005) Eur. J. Cell Biol. 84, 279-94). No molecular function or catalytic activity has been ascribed to Mina53.

None of the literature on Mina53 describes a method for expressing and purifying Mina53. The functional assays such as localization and immunoprecipitation carried out in the art do not require purified protein.

The 2-oxoglutarate (2-OG) and ferrous iron dependent oxygenases are a superfamily of enzymes that catalyse a wide range of reactions including hydroxylations, desaturations and oxidative ring closures (Hausinger (2004), Crit. Rev. Biochem. Mol. Biol. 39, 21-68; Ryle & Hausinger (2002) Curr. Opin. Chem. Biol. 6, 193-201; and Schofield et al. (1999) Journal of Inorganic Biochemistry 74, 49-49). Substrate oxidation is coupled to conversion of 2-OG to succinate and carbon dioxide. At least in some cases, binding of oxygen is followed by the oxidative decarboxylation of 2-OG to give succinate, $CO_2$ and a ferryl species $[Fe(IV)=O]$ at the iron centre. This highly reactive intermediate can then oxidize an unactivated C—H bond in the prime substrate, e.g. the oxidation of prolyl or asparaginyl residues in human proteins, or effect other oxidative reactions. Evidence for intermediates comes from substrate-analogue studies, model compounds and spectroscopic analyses.

The sequential binding of co-substrate and prime substrate, which is necessary to trigger oxygen binding, is probably important to limit the generation of reactive oxidizing species in the absence of prime substrate. The generation of such species in a prime-substrate-uncoupled manner can inactivate 2-oxoglutarate and the related oxygenases through self-oxidation, which sometimes leads to fragmentation. Typically, the uncoupled turnover of 2-OG occurs at approximately 5% of the rate of its coupled turnover in the presence of saturating concentrations of prime substrate, although it can also occur at a lower or higher rate.

Several 2-OG-dependent oxygenases, including procollagen prolyl hydroxylase, the hypoxia inducible factor prolyl hydroxylases, and anthocyanidin synthase, also have a requirement for ascorbate for full catalytic activity. Although ascorbate might stimulate activity by reducing $Fe^{3+}$, or other high valent form of iron, to $Fe^{2+}$ (either free in solution or at the active site), the stimulation of oxygenase activity by ascorbate might occur by other mechanisms, for instance, by promoting completion of uncoupled cycles. For uncoupled reaction cycles that are catalysed by procollagen prolyl hydroxylase in the absence of prime substrate, the oxidation of 2-OG to succinate has been shown to be stoichiometrically coupled to ascorbate. It is believed that one role of ascorbate is to function as a surrogate reducing substrate to 'rescue' the enzyme in the event of the uncoupled production of a ferryl $[Fe(IV)=O]$ intermediate.

Studies with several enzymes have shown that certain substrate analogues and mutants can also stimulate uncoupled 2-OG turnover. It is also known in the literature that reducing agents other than ascorbate itself can act as reducing agents in the uncoupled turnover reaction, including derivatives of ascorbate (Zhang et al (1995) Biochem. J. 307 (Pt 1), 77-85 and Myllyla et al. (1978) Biochem. Biophys. Res. Commun. 83, 441-8).

SUMMARY OF THE INVENTION

The present inventors have successfully purified recombinant Mina53 and demonstrated that the purified recombinant Mina53 functions as a 2-oxoglutarate (2-OG) dependent oxygenase. In particular, the inventors have devised a method for expressing and purifying both full-length and truncated Mina53 in using a bacterial expression system. The inventors have also demonstrated for the first time that Mina53 is a 2-OG dependent oxygenase.

Accordingly, the present invention provides:

a method for assaying oxygenase activity, the method comprising monitoring oxygenase activity of Mina53;

a method for identifying an inhibitor of Mina53 oxygenase activity, the method comprising:

contacting a Mina53 polypeptide with a test agent under conditions suitable for oxygenase activity; and monitoring for oxygenase activity;

a method for identifying a substrate of Mina53, the method comprising:

contacting a Mina53 polypeptide with a test substrate under conditions suitable for oxygenase activity; and monitoring for oxygenase activity;

the use of recombinant Mina53 in an assay for oxygenase activity;

the use of an inhibitor of Mina53 oxygenase activity in the manufacture of a medicament for use in treating cancer;

a method of treating cancer in an individual in need thereof, the method comprising administering to the individual a therapeutic amount of an inhibitor of Mina53 oxygenase activity;

a method of inhibiting cell proliferation, the method comprising contacting cells in vivo or in vitro with an inhibitor of Mina53 oxygenase activity; and a method for purifying a Mina53 polypeptide, the method comprising:

culturing host cells comprising an expression vector encoding Mina53 such that Mina53 is expressed; and isolating Mina53 from the cells.

BRIEF DESCRIPTION OF THE FIGURES

FIGS. 1A and 1B are an alignment of the amino acid sequence of Mina53, NO66 and factor inhibiting hypoxia inducible factor (1H2K).

BRIEF DESCRIPTION OF THE SEQUENCES

SEQ ID NO: 1 is the nucleotide and amino acid sequence of human Mina53.

SEQ ID NO: 2 is the amino acid sequence of human Mina53.

SEQ ID NO: 3 is the nucleotide and amino acid sequence of human NO66.

SEQ ID NO: 4 is the amino acid sequence of human NO66.

DETAILED DESCRIPTION OF THE INVENTION

The present invention relates to the purification of recombinant Mina53 and to identification of Mina53 as a 2-oxoglutarate (2-OG) dependent oxygenase and provides for the use of Mina53 in assay methods to identify modulators of Mina53 oxygenase activity and substrates that are hydroxylated by Mina53.

In one aspect of the invention, Mina53 or a variant or fragment thereof for use in accordance with the invention has the ability to convert 2-OG to succinate and carbon dioxide.

Preferably, Mina53 for use in a method of the invention comprises:

(a) the amino acid sequence of SEQ ID NO: 2;

(b) a variant thereof having at least 50% identity to the central JmjC domain of Mina53 encompassed by the amino acid sequence of SEQ ID NO: 2 between amino acids 128 and 265 or 128 and 271 and having oxygenase activity; or (c) a fragment of either thereof having oxygenase activity.

A variant or an active fragment of Mina53 may typically be identified by monitoring for 2-OG oxygenase activity as described in more detail below. The variant of Mina53 has at least 50% sequence identity, for example at least 55% sequence identity, with the sequence of Mina53 in the central JmjC domain (amino acids 128 and 265 or 128 and 271 in SEQ ID NO: 2) or double-stranded B-helix domain (amino acids 161 to 265 in SEQ ID NO: 2). The variant may have at least 35%, for example at least 50% or 60% sequence identity with the amino acid sequence of SEQ ID NO: 2 over its entire length, typically greater than 70% or 80%, more typically greater than about 90% or 95% sequence identity.

The variant may be a homologue of Mina53 such as NO66 (Eilbracht et al. (2003), Eur. J. Biol. 84:279-294). The homologue is generally a human protein, but homologues from other species may be used.

The amino acid sequence of NO66 is shown in SEQ ID NO: 4. The Mina53 polypeptide used in an assay of the invention may be a variant or fragment of SEQ ID NO: 4, which variant or fragment retains 2-OG oxygenase activity. The variant may have at least 60%, such as at least 70%, 80%, 90% or 95% sequence identity with the amino acid sequence of SEQ ID NO: 4.

Sequence identity may be calculated using any suitable algorithm. For example, the UWGCG Package provides the BESTFIT program can be used to calculate homology (for example used on its default settings) (Devereux et al. (1984) *Nucleic Acids Research* 12, p 387-395). The PILEUP and BLAST algorithms can be used to calculate homology or line up sequences (typically on their default settings), for example as described in Altschul (1993) J. Mol. Evol. 36:290-300; Altschul et al. (1990) J. Mol. Biol. 215:403-10.

Such variants may include allelic variants and the deletion, modification or addition of single amino acids or groups of amino acids within the protein sequence, as long as the peptide retains 2-OG oxygenase activity.

Amino acid substitutions may be made, for example from about 1, 2 or 3 to about 10, 20 or 30 substitutions. Conservative substitutions may be made, for example according to the following Table. Amino acids in the same block in the second column and preferably in the same line in the third column may be substituted for each other.

| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

Variant polypeptides within the scope of the invention may be generated by any suitable method, for example by gene shuffling (molecular breeding) techniques.

The present invention also includes use of active portions, fragments, derivatives and functional mimetics of the polypeptides of the invention. An "active portion" of a polypeptide means a peptide which is less than said full-length polypeptide, but which retains 2-OG oxygenase activity. Such an active fragment may be included as part of a fusion protein, e.g. including a binding portion for a different i.e. heterologous ligand.

The fragment may have at least about 50 amino acids or up to about 60, 70, 80, 100, 150, 200, 300 or 400 amino acids. In particular, but not exclusively, this aspect of the invention encompasses the situation when the protein is a fragment of the complete Mina53 protein sequence and may represent a catalytic region, capable of converting 2-OG to succinate and carbon dioxide. The fragment may comprise the region from about amino acid 161 to 265, for example from about amino acid 128 to about 265 or about 271 of the amino acid sequence shown in SEQ ID NO: 2. Useful fragments include C-terminal truncated fragments such as fragments comprising residues 1 to 301 shown in SEQ ID NO: 2, fragments comprising an N-terminal deletion, such as fragments comprising residues 26 to 465 of the amino acid sequence shown in SEQ ID NO: 2 and fragments comprising both N-terminal and C-terminal truncations, such as fragment comprising residues 40 to 239 of the amino acid sequence shown in SEQ ID NO: 2. Other suitable fragments may readily be identified, for example by comparing the Mina53 amino acid sequence to the amino acid sequence of one or more known 2-OG dependent oxygenase and identifying which regions are not homologous to regions having catalytic activity. Such fragments can be used to construct chimeric molecules.

The equivalent fragments of SEQ ID NO: 4 having oxygenase activity may also be used in an assay of the invention and are encompassed within the term "Mina53" used herein.

The Mina53 polypeptides may be synthetically prepared. The polypeptides may be chemically or biochemically modified, e.g. post-translationally modified. For example, they may be glycosylated or comprise modified amino acid residues. They may also be modified by the addition of histidine residues (typically six), or other sequence tag such as a maltose binding protein tag or intein tag, to assist their purification or by the addition of a nuclear localisation sequence to promote translocation to the nucleus or by post translational modification including hydroxylation or phosphorylation. Polypeptides of the invention may be GST fusion polypeptides. Such modified polypeptides fall within the scope of the term "Mina53".

The polypeptides of the invention may be present in a substantially isolated form. They may be mixed with carriers or diluents which will not interfere with their intended use and still be regarded as substantially isolated. They may also be in a substantially purified form, in which case they will generally comprise at least about 90%, e.g. at least about 95%, 98% or 99%, of the proteins, polynucleotides, cells or dry mass of the preparation.

The polypeptides of the invention may be used in assays for 2-OG dependent oxygenase activity, for example to identify modulators, preferably inhibitors of hydroxylase activity. The inhibitors may be selective inhibitors. The polypeptides of the invention may also be used in structural analyses such as crystallography.

The Mina53 polypeptides may be used in assays for 2-OG oxygenase activity in the absence of a prime substrate. The Mina53 polypeptides may also be used to determine oxygenase activity in the presence of one or more suitable substrates.

Mina53 used in a method of the invention may be recombinant Mina53 or naturally occurring Mina53. Preferably, recombinant Mina53 is used. Recombinant Mina53 may be produced using standard expression vectors that comprise nucleotide sequences encoding Mina53. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for protein expression. Other suitable vectors would be apparent to persons skilled in the art. By way of further example in this regard we refer to Sambrook et al. 1989.

Methods of the invention may utilise cells that have been modified to express a Mina53 polypeptide as defined herein. The Mina53 may also be present in a cell extract or in a partially or substantially purified form.

A polypeptide in a partially or substantially purified form, is generally comprised in a preparation in which more than 50%, e.g. more than 80%, 90%, 95% or 99%, by weight of the polypeptide in the preparation is a polypeptide of the invention.

Methods for Obtaining Purified Mina53

The present inventors tried a number of standard approaches to obtain soluble, active recombinant Mina53 in purified form from *E. coli*. The standard approaches tested have not been successful. However, the present inventors have now found that it is possible to express a recombinant Mina53 in soluble and highly active form using a modified expression and purification method. The inventors have also demonstrated that Mina53 is a 2-OG dependent oxygenase. Accordingly, the invention provides a method for obtaining purified Mina53. Purified Mina53 obtainable by this method is also provided.

Mina53 may be obtained by introducing an expression vector comprising a polynucleotide encoding Mina53 into a host cell. The polynucleotide may comprise the coding region of the nucleotide sequence of SEQ ID NO: 1 or be a fragment or variant of the coding region of the nucleotide sequence shown in SEQ ID NO: 1. The fragment may lack one or more nucleotide from the 5' or 3' end of the coding region, for example which lacks at least about 150 nucleotides, for example between about 300 and about 690, between about 450 and about 600 nucleotides, between about 510 and about 570, or between about 525 and about 555. The variant typically has at least about 70%, 80%, 90%, 95%, 98% or 99% sequence identity to the coding region of the nucleotide sequence of SEQ ID NO: 1 over a region of at least about 588 contiguous nucleotides, for example 588 contiguous nucleotides at the 3' end of the coding region shown in SEQ ID NO: 1. Sequence identity may be determined by any suitable method, for example, as described above.

Expression vectors are routinely constructed in the art and may for example involve the use of plasmid DNA and appropriate initiators, promoters, enhancers and other elements, such as for example polyadenylation signals which may be necessary and which are positioned in the correct orientation in order to allow full protein expression. Suitable vectors would be very readily apparent to those of skill in the art. Promoter sequences may be inducible or constitutive promoters depending on the selected assay format. The promoter may be tissue specific. Thus the coding sequence in the vector is operably linked to such elements so that they provide for expression of the coding sequence (typically in a cell). The term "operably linked" refers to a juxtaposition wherein the components described are in a relationship permitting them to function in their intended manner.

The vector may be, for example, a plasmid, virus or baculovirus vector. The vector is typically adapted to be used in a bacterial cell, such as *E. coli*. The vector may have an origin of replication. The vector may comprise one or more selectable marker genes, for example an ampicillin resistance gene in the case of a bacterial plasmid or a resistance gene for a fungal vector. Vectors may be used to transfect or transform a host cell, for example, a bacterial host cell, fungal host cell, a mammalian, e.g. human host cell or a bacillovirus host cell. The bacterial host cell is preferably a strain of *E. coli*, for example BL21 (DE3).

A method of producing a purified Mina53 polypeptide is provided by the invention. The method typically comprises culturing host cells comprising an expression vector encoding Mina53 and isolating the Mina53 polypeptide from the cells. The host cells may be cultured, for example, at a temperature of from about 15° C. to about 37° C. The polypeptide may be isolated by lysing the cells and extracting the protein from the lysis buffer. The lysis buffer typically comprises from about 250 mM to about 700 mM salt, e.g. NaCl, such as from about 400 mM to about 600 mM, e.g. 500 mM. A method of producing a Mina53 polypeptide according to the invention may further comprise introducing a polynucleotide or vector according to the invention into the host cell. The Mina53 polypeptide is comprised in the soluble fraction obtained upon lysis of the cell culture. The polypeptide may be further purified from the soluble fraction, for example by affinity purification, such as via an affinity tag fused to the truncated 2-OG dependent oxygenase.

Methods for introducing polypeptides and vectors into host cells are well known in the art, and include electroporation and heat shock techniques without limitation. Expression of the truncated polypeptide may then be achieved by culturing the host cells at a suitable temperature. The cells expressing recombinant Mina53 are preferably kept at between about 15° C. and about 30° C., for example at about 20° C. or about 28° C. to induce expression of recombinant Mina53. Where the host cells are bacteria, such as *E. coli*, the cells may be cultured in 2TY medium. IPTG may be added to the culture medium, either throughout the period of incubation (or growth period) or in the final stages of the incubation period.

The lysis buffer containing a high salt level is typically used to lyse the cells after centrifuging the cells to remove the cell culture medium. The buffer typically contains from about 250 mmol salt, e.g. NaCl, to about 700 mmol salt, for example from about 400 to about 600 mmol NaCl, such as about 500 mmol NaCl. The extraction buffer may comprise detergents, such as Triton X-100 and/or SDS (typically 1%), and/or lysozyme. Glycerol may be present in the lysis buffer, typically at a concentration of from about 5% to about 20%, such as about 10%. The lysis buffer typically has a pH greater than about 7.5, for example from about 7.6 to about 8.1, from about 7.8 to about 8.0, more preferably about 7.9. The lysis buffer may be suitable for sonication of the cells. Tris may also be present in the lysis buffer, for example at a concentration of from about 10 mmol to about 100 mmol, such as about 20 mmol.

After lysis, the cells may be centrifuged. After centrifugation, the supernatant represents the soluble fraction. The concentration of proteins present in the soluble fraction depends on the quantity of extraction buffer used. The Mina53 is present in the soluble fraction in an amount sufficient for the truncated enzyme to be purified. This can be determined by SDS PAGE. If it is possible to detect the truncated enzyme by SDS PAGE, there is sufficient enzyme present for purification.

Mina53 polypeptides of the invention may be purified by standard techniques known in the art. For example, where the polypeptide comprises a his tag, it may be purified using a his-binding resin by following the manufacturer's instructions (e.g. Novagen). The purification procedure may comprise the following steps. The cells expressing a recombinant polypeptide of the invention may be pelleted and resuspended in a suitable buffer and then sonicated to break up the cells. The cell debris is separated from the soluble material by centrifugation and the soluble fraction is loaded on a his-bind column. After washing the column with binding buffer and wash buffer, the bound protein is eluted from the column using elution buffer. The binding, wash and elution buffers each typically comprise 0.5M NaCl. It is not necessary to add additional salt. The eluted protein is then concentrated and incubated with thrombin (typically at a concentration of 1 $Umg^{-1}$ at 4° C. for 16 hours). The digested proteins are separated using a gel filtration column and the Mina53 eluted from the column is generally at least 90%, or at least 95% pure. The purified protein for use in the various assays described herein may be de-salted.

Assays

Our data shows that Mina53 catalyses the conversion of 2-OG to succinate and carbon dioxide. This newly discovered activity of Mina53 means that, for the first time, assays for identifying inhibitors of Mina53 activity may be performed. Blocking 2-OG oxygenase activity of Mina53 will inhibit cell proliferation and hence inhibitors of 2-OG oxygenase activity will be useful in treating cancer.

We describe below in more detail a number of different assays that may be carried out to identify modulators of Mina53 oxygenase activity and in particular of 2-OG oxygenase activity. Typically, the assays utilise a human Mina53 polypeptide as described herein. Mina53 polypeptides may be provided either in purified or unpurified form, for example, as cellular extracts or by purification of the relevant polypeptides from such extracts. Alternatively, the relevant component can be expressed using recombinant expression techniques and purified for use in the assay. Alternatively, the components may be expressed recombinantly in a cell for use in cell based assays.

Assay Methods

The Mina53 polypeptides may be used in an assay for oxygenase activity, such as 2-OG oxygenase activity. These polypeptides are also useful in assays for identifying an agent which modulates, such as inhibits, Mina53 oxygenase activity. The method comprises contacting a Mina53 polypeptide and a test substance, such as a potential inhibitor, in the presence of one or more co-substrate and optionally a prime substrate. Suitable co-substrates include oxygen, for example, dioxygen, and 2-oxoacids such as 2-OG. Preferably, the co-substrate is 2-OG. In addition to oxygen or a 2-oxoacid, a reducing agent, such as ascorbate may also be used as a co-substrate. The components of the assay are contacted under conditions in which the enzyme acts on the co-substrate in the absence of the test substance and determining the extent of co-substrate modification. Alternatively, hydroxylation of the prime substrate may be monitored. Assays that detect binding to Mina53 in the absence of catalytic turnover may also be used. Such assays may employ techniques such as NMR, MS or fluorescence spectroscopy. The co-substrate may be modified, e.g. 2-OG, or consumed, e.g. oxygen or ascorbate, by Mina53. The assay may also be used to detect substances that increase the activity of the 2-OG dependent oxygenase by assaying for increases in activity. Suitable assays have been described in the art for other 2-OG dependent oxygenases.

Such assays of the present invention may be used to identify inhibitors of oxygenase activity and are thus preferably carried out under conditions under which Mina53 is active as an oxygenase in the absence of the test substance. The Mina53 oxygenase activity in the presence of the test substance is compared to Mina53 oxygenase activity in the absence of the test substance to determine whether the test substance is an inhibitor of Mina53 oxygenase activity. In the alternative, the assays may be used to look for promoters of Mina53 oxygenase activity, for example, by looking for increased conversion of co-substrate and/or hydroxylation of substrates compared to assays carried out in the absence of a test substance. The assays may also be carried out under conditions in which oxygenase activity is reduced or absent, such as under hypoxic conditions, and the presence of activity or increase in activity could be monitored under such conditions.

The assays of the invention may also be used to identify inhibitors or activators which are specific for Mina53 and which do not have activity or are less active with other 2-OG oxygenases, for example, such as hypoxia inducible factor (HIF) asparagine or prolyl hydroxylases. Conversely, the assays of the invention may be used to identify inhibitors or activators specific for one or more 2-OG dependent oxygenase, for example, such as HIF asparagine or prolyl hydroxylases, which do not inhibit Mina53.

The assays of the invention may also be used to identify inhibitors or activators which are specific for Mina53 activity at a particular substrate or residue within a substrate.

In medicinal applications, for example, it is advantageous to modulate oxygenase activity of a single enzyme or group of enzymes. Assays of the invention may therefore be use to identify agents which selectively modulate activity of Mina53 relative to a second 2-OG dependent oxygenase, including but not limited to the HIF hydroxylases, including FIH, PHD1, PHD2 and PHD3, AlkB, ABH1, ABH2, ABH3, procollagen prolyl and lysyl hydroxylases, the phosphotidylserine receptor and 2-OG oxygenases that have been characterized as JmjC proteins according to the SMART database.

The invention provides for the use of such selective inhibitors in the manufacture of a medicament for the treatment of a condition associated with altered, i.e. enhanced or reduced, 2-OG dependent oxygenase activity, such as Mina53 oxygenase activity.

It is also possible, using the method of the invention to identify selective inhibitors when the substrate of one or more of the enzymes being tested is unknown. In this embodiment, generally it will be one or more of the enzymes that it is wished not to inhibit that has an unknown substrate. The effect of a test agent on activity of an oxygenase may be determined in the absence of a substrate by determining whether or not the test agent affects, for example inhibits or stimulates, the rate of turnover of 2-OG by the oxygenase.

The assays of the present invention may use a substrate that is hydroxylated or otherwise oxidised by Mina53. In particular, such substrates may be used in assays to monitor for the activity of a modulator of Mina53 2-OG oxygenase activity. The substrate may be a peptide or nucleic acid substrate.

Any suitable substrate which is hydroxylated by Mina53, with Mina53 typically having the amino acid sequence of SEQ ID NO: 2, may be used. Some substrates of 2-OG dependent oxygenases are well known in the art. The substrate may be a naturally occurring protein or a recombinant or synthetic protein or a nucleic acid. Fragments and variants of naturally occurring substrate proteins or nucleic acids which include the site of oxidisation by Mina53 may be used as substrates in the assay of the invention.

The methods of the invention may be used to detect novel substrates of Mina53 2-OG dependent oxygenase activity. In such an assay a test substrate is used and the detection of hydroxylase activity indicates that hydroxylation of the test substrate has occurred and, accordingly, that the test substrate is a substrate of the Mina53.

Methods for Monitoring Modulation

The precise format of any of the screening or assay methods of the present invention may be varied by those of skill in the art using routine skill and knowledge. The skilled person is well aware of the need to additionally employ appropriate control experiments. The assays of the present invention may involve monitoring for hydroxylation of a suitable substrate, monitoring for the utilisation of substrates and co-substrates, monitoring for the production of the expected products between the enzyme and its substrate. Assay methods of the present invention may also involve screening for the direct interaction between components in the system. Alternatively, assays may be carried out which monitor for downstream effects mediated by the substrate, such as substrate mediated transcription using suitable reporter constructs or by monitoring for the upregulation of genes or alterations in the expression patterns of genes know to be regulated directly or indirectly by the substrate.

Various methods for determining hydroxylation either directly or indirectly are known in the art. Any suitable method may be used for determining 2-OG dependent oxygenase activity of Mina53 such as by substrate or co-substrate utilisation, product appearance such as peptide hydroxylation or down-stream effects mediated by hydroxylated or non-hydroxylated products.

The substrate, enzyme and potential inhibitor compound may be incubated together under conditions which, in the absence of inhibitor provide for hydroxylation of the substrate, and the effect of the inhibitor may be determined by determining hydroxylation of the substrate. This may be accomplished by any suitable means. Small polypeptide substrates may be recovered and subjected to physical analysis, such as mass spectrometry or chromatography, or to functional analysis. Such methods are known as such in the art and may be practiced using routine skill and knowledge. Determination may be quantitative or qualitative. In both cases, but particularly in the latter, qualitative determination may be carried out in comparison to a suitable control, e.g. a substrate incubated without the potential inhibitor.

In alternative embodiments, reporter constructs may be provided in which promoters mediated by a substrate are provided operably linked to a reporter gene. Any suitable reporter gene could be used, such as for example enzymes which may then be used in colorometric, fluorometric, fluorescence resonance or spectrometric assays.

In the assay methods described herein, typically the Mina53 and the substrate are contacted in the presence of a co-substrate, such as oxygen and/or a 2-oxoacid, such as 2-OG and/or dioxygen. Hydroxylase activity may be determined by determining turnover of one or more of the co-substrates, such as oxygen, 2-OG and/or ascorbate. This may be achieved by determining the presence and/or amount of reaction products, such as hydroxylated substrate or succinic acid. The amount of product may be determined relative to the amount of substrate. For example, in such embodiments the substrate may be a polypeptide and, for example, the product measured may be hydroxylated polypeptide. For example, the extent of hydroxylation may be determined by measuring the amount of hydroxylated polypeptide, succinate or carbon dioxide generated in the reaction, or by measuring the depletion of 2-OG or dioxygen. Methods for monitoring each of these are known in the scientific literature, for example in Myllyhaiju J. et al. EMBO J. 16 (6): 1173-1180 (1991) or as in Cunliffe C. J. et al. Biochem. J. 240 617-619 (1986).

Unused 2-OG may be derivatised by chemical reagents, exemplified by but not limited to hydrazine derivatives and ortho-phenylene diamine derivatives, to give indicative chromophores or fluorophores that can be quantified and used to indicate the extent of hydroxylation of the test polypeptide. Dissolved oxygen electrodes, exemplified by but not limited to a "Clarke-type" electrode or an electrode that uses fluorescence quenching, may be used to follow the consumption of oxygen in an assay mixture, which can then be used to indicate the extent of hydroxylation of the test polypeptide in an analogous manner to the above.

The fluorescent product of the reaction of ortho-phenylenediamine (OPD) with the α-ketoacid motif of 2-OG is 3-(2-Carboxyethyl)-2(1H)-quinoxalinone. This fluorescent product can be readily detected by standard equipment such as that manufactured by for example Molecular Devices, Tecan, BMG Labtechnologies, Jasco and Perkin Elmer and there is extensive precedent demonstrating that the production of fluorescent products can be used in high-throughput screens.

The fluorescent product is generally detected with the excitation filter set as from about 300 nm to about 400 nm, preferably from about 335 to about 345 nm, most preferably at about 340 nm. The emission filter is generally at from about 400 to about 450 nm, preferably from about 415 to about 425 nm, most preferably at about 420 nm.

This assay procedure lends itself to high-throughput formats, such as multi-well plate formats e.g. 96-, 384-, or 1536-well plate formats.

Further, the nature of the fluorescent product can be tuned by modifying the nature of the derivatisation reagent used. For example, the sensitivity of the method may be increased by using either 1,2-dimethoxy-4,5-diaminobenzene, or 1,2-methylenedioxy-4,5-diaminobenzene.

The precise format of any of the screening or assay methods of the present invention may be varied by those of skill in the art using routine skill and knowledge. The skilled person is well aware of the need to additionally employ appropriate control experiments. Activity is measured by derivatisation of 2-OG with OPD or other aromatic diamines, such as 1,2-dimethoxy-4,5-diaminobenzene or 1,2-methylenedioxy-4,5-diaminobenzene, such that the derivative gives improved sensitivity compared to use of OPD (Mühling et al Journal of Chromatography B (2003) 383-392, Nakamura et al. Chem. Pharm Bull. (1987) 687-692).

The assay is carried out under conditions suitable for hydroxylation of the substrate by the hydroxylase. Accordingly, 2-OG is present in the assay. The assay mixture may also contain iron, preferably ferrous iron.

Other components may be added to the assay mixture. For example, a reducing agent such as ascorbate, a thiol such as dithiothrietol (DDT), β-mercaptoethanol, N-acetylcysteine or phenol may be added to the assay to help maintain enzyme structure and/or catalase may be added to destroy any $H_2O_2$ that might be produced. However, the assay will work in the absence of a reducing agent or catalase.

The assay is typically carried out at a temperature of from about 25° C. to about 40° C., for example at a temperature of from about 30° C. to about 39° C., or from about 35° C. to about 38° C. or about 37° C. The pH of the assay mixture is typically between about pH 7 to about pH 9, for example from about pH 7.5 to about pH 8. Suitable buffers, such as Tris or HEPES, may be used to maintain the pH of the assay mixture.

Typically, the assay is carried out under normoxic conditions. The assay may also be carried out under conditions in which hydroxylation is reduced or absent, such as under hypoxic conditions, in order to detect modulation of oxygenase activity by an agent which enhances hydroxylation.

Alternatively, the end-point determination may be based on conversion of the polypeptide substrate or peptide fragments (including synthetic and recombinant peptides) derived from the polypeptide substrate into detectable products. Peptides may be modified to facilitate the assays so that they can be rapidly carried out and may be suitable for high throughput screening.

For example, reverse phase HPLC (C-4 octadecylsilane column), as exemplified herein, may be used to separate starting synthetic peptide substrates for HIF hydroxylase from the hydroxylated products. The latter typically have a shorter retention time in the column. Modifications of this assay or alternative assays for HIF hydroxylase activity may employ, for example, mass spectrometric, spectroscopic, and/or fluorescence techniques as are well known in the art (Masimirembwa C. et al. Combinatorial Chemistry & High Throughput Screening (2001) 4 (3) 245-263, Owicki J. (2000) J. Biomol. Screen. 5 (5) 297-305, Gershkovich A et al. (1996) J. Biochem. & Biophys. Meths. 33 (3) 135-162, Kraaft G. et al. (1994) Meths. Enzymol. 241 70-86). Fluorescent techniques may employ versions of the substrate modified in such as way as to carry out or optimise spectroscopic or fluorescence assays.

Binding of a molecule which discriminates between the hydroxylated and non-hydroxylated form of a polypeptide or other substrate may be assessed using any technique available to those skilled in the art, which may involve determination of the presence of a suitable label.

Assay methods of the present invention may also take the form of an in vivo assay. The in vivo assay may be performed in a cell line such as a yeast or bacterial strain in which the relevant polypeptides or peptides are expressed from one or more vectors introduced into the cell.

Test Compounds

Agents which may be screened using the assay methods described herein may be natural or synthetic chemical compounds used in drug screening programmes. Extracts of plants, microbes or other organisms which contain several characterised or uncharacterised components may also be used.

Combinatorial library technology (including solid phase synthesis and parallel synthesis methodologies) provides an efficient way of testing a potentially vast number of different substances for ability to modulate an interaction. Such libraries and their use are known in the art, for all manner of natural products, small molecules and peptides, among others. The use of peptide libraries may be preferred in certain circumstances.

Potential inhibitor compounds (i.e. antagonists) may be polypeptides, small molecules such as molecules from commercially available combinatorial libraries, or the like. Small molecule compounds which may be used include 2-OG analogues, or substrate analogues, which inhibit the action of the enzyme. Small molecule compounds, and other types of compound, that may be used include all known 2-OG oxygenase inhibitors such as those known to inhibit HIF hydroxylases (see for example WO02/074981 and WO03/080566) and procollagen prolyl hydroxylases.

Potential promoting agents may be screened from a wide variety of sources, particularly from libraries of small compounds which are commercially available. Oxygen-containing compounds may be included in candidate compounds to be screened, for example 2-OG analogues.

A test compound which increases, potentiates, stimulates, disrupts, reduces, interferes with or wholly or partially abolishes hydroxylation of the substrate and which may thereby modulate activity, may be identified and/or obtained using the assay methods described herein.

Agents which increase or potentiate hydroxylation (i.e. agonists), for example prolyl or asparaginyl hydroxylation, may be identified and/or obtained under conditions which, in the absence of a positively-testing agent, limit or prevent hydroxylation. Such agents may be used to potentiate, increase, enhance or stimulate the oxygenase activity of Mina53.

In various aspects, the present invention provides an agent or compound identified by a screening method of the invention to be a modulator of Mina53 oxygenase activity e.g. a substance which inhibits or reduces, increases or potentiates the activity of Mina53.

Following identification of a modulator, the substance may be purified and/or investigated further (e.g. modified) and/or manufactured. A modulator may be used to obtain peptidyl or non-peptidyl mimetics, e.g. by methods well known to those skilled in the art and discussed herein. A modulator may be modified, for example to increase selectively, as described herein. It may be used in a therapeutic context as discussed below.

For therapeutic treatment, the modulator may be used alone or in combination with any other therapeutically active substance or treatment. For example, for anti-tumour therapy another anti-tumour compound or treatment, such as radiotherapy or chemotherapy, may be used in combination with the modulator.

The compounds which are acids can be present in the form of salts, such as sodium salts. The compounds may also be present in the form of derivatives such as the dimethyl ester, diethyl ester, monoethyl ester or di- or mono-amide. In certain instances these derivatives may be preferred, for example when inhibition of the enzyme within a cell of an organism is required.

Compounds which modulate 2-OG oxygenases may be useful as agents of the invention, or may be used as test substances in an assay of the invention. The test compound may, for example, be an inhibitor of procollagen prolyl hydroxylase, hypoxia inducible factor prolyl and asparaginyl hydroxylases or gibberellin C-20 oxidase. N-oxaloglycine and its derivatives are suitable examples. Compounds which modulate 2-OG oxygenases, and families of such compounds, are known in the art, for example in Aoyagi et al. (2002) Hepatology Research 23 (1): 1-6, Aoyagi et al. (2003) Free Radical Biology and Medicine 35:410 Suppl. 1, Philipp et al. (2002) Circulation 106 (19): 1344 Suppl. S, Ivan et al. (2002) PNAS USA 99 (21): 13459-13464, Nwogu et al. (2001) Circulation 104 (18): 2216-2221, Myllyharju and Kivirikko (2001) Ann Med 33 (1): 7-21, Ohta et al. (1984) Chemical and Pharm Bulletin 32 (11): 4350-4359, Franklin et al. (2001) Biochem J. 353: 333-338, Franklin (1997) Int J. Biochem Cell Biol 29 (1): 79-89, Dowell et al. (1993) Eur J Med Chem 28 (6): 513-516, Baader et al (1994) Biochem J. 300: 525-530, Baader et al. (1994) Eur J Clin Chem and Clin Biol 32 (7): 515-520, Bickel et al. (1998) Hepatology 28 (2): 404-411, Bickel et al. (1991) J. Hepatology 13: S26-S34 Suppl. 3, U.S. Pat. No. 6,200,934, U.S. Pat. No. 5,916,898, US Patent Applications 2003-0176317, 2003-0153503 and 2004-0053977, WO 02/074981, WO 03/080566, WO 04/035812, Cunliffe et al. (1992) J. Med. Chem. 35:2652-2658, Higashide et al. (1995) J. Antibiotics 38:285-295, Cunliffe et al. (1986) Biochem. J. 239(2):311-315, Franklin et al. (1989) Biochem. J. 261(1):127-130, Friedman et al. (2000) PNAS USA 97(9):4736-4741, Wu et al. (1999) J. Am. Chem. Soc. 121(3): 587-588, DE-A-3818850, Wang et al (2001) Biochemistry US:15676-15683 and Lerner et al. (2001) Angew Chem. Int. Edit. 40:4040-4041.

Suitable test compounds are disclosed in WO03/080566 and WO02/074981. Other suitable test compounds include compounds of formula (I):

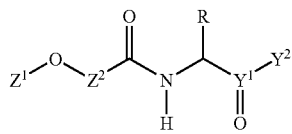

wherein
- Y² is selected from —OR' and —NR'R" wherein R' is hydrogen, or unsubstituted C₁₋₄ alkyl and R" is hydrogen, hydroxy or unsubstituted C₁₋₄ alkyl;
- Y¹ is selected from —C—, —S— and —S(O)—;
- Z² is selected from —C(O)— and —NR"— wherein R" is selected from hydrogen, hydroxy or unsubstituted C₁₋₄ alkyl;
- Z¹ is selected from hydrogen and unsubstituted C₁₋₄ alkyl; and
- R is a side chain of a naturally occurring amino acid.

Preferably Y¹ is —C— and Y² is —OH or —NH₂. Most preferably Y¹ is —C— and Y² is —OH.

Preferably Z² is —C(O)— or —NR"— wherein R" is hydrogen, methyl or ethyl. More preferably Z² is —C(O)— or —NH—. Preferably Z¹ is hydrogen, methyl or ethyl, more preferably hydrogen. Most preferably Z² is —C(O)— and Z¹ is hydrogen, methyl or ethyl.

Preferably R is a side chain of alanine, valine, leucine or phenylalanine. Preferably R is a side chain of valine, leucine or phenylalanine. More preferably R is a side chain of phenylalanine, i.e. —CH₂Ph.

L-stereoisomers or D-stereoisomers of these compounds may be used.

An exemplary synthetic scheme used to obtain test compounds of formula (I) is shown below in Scheme 1. Here an amino acid is reacted with an oxalyl chloride in order to produce a compound of formula (I). In this scheme the amino acid used is phenylalanine, although it will be apparent that the same general reaction will occur with other amino acids. The first reaction yields a protected compound of the invention (the dimethyl ester form). The diacid form is easily generated through reaction with aqueous sodium hydroxide.

Scheme 1:

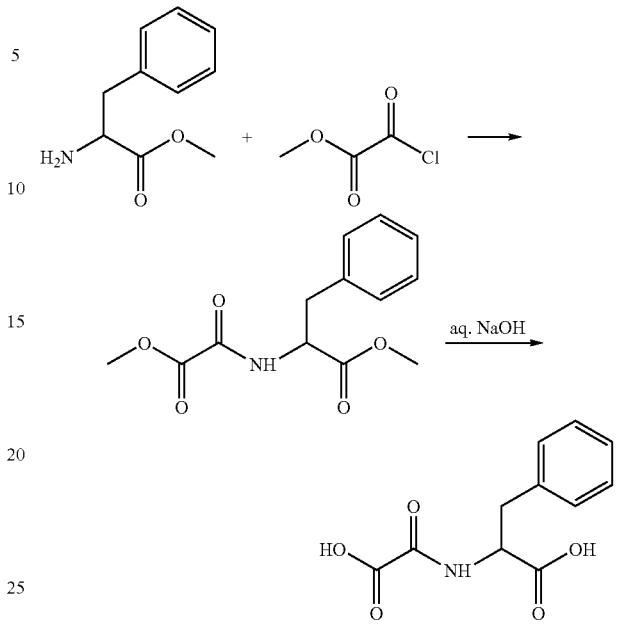

Compounds in which X is —O— or —S— or Z is other than —CO—CO—OH may by synthesised as described in Mole et al. (2003) Bioorg. Med. Chem. Lett. 13, 2677-2680 and Cunliffe et al. J. Med. Chem. (1992) 35 2652-2658.

Therapeutic Applications

A compound, substance or agent which is found to have the ability to affect the oxygenase activity of Mina53 has therapeutic and other potential in a number of contexts, as discussed. For therapeutic treatment, such a compound may be used alone or in combination with any other active substance, e.g. for anti-tumour therapy with another anti-tumour compound or therapy, such as radiotherapy or chemotherapy.

An agent identified using one or more primary screens (e.g. in a cell-free system) as having ability to modulate hydroxylase activity may be assessed further using one or more secondary screens.

Generally, an agent, compound or substance which is a modulator according to the present invention is provided in an isolated and/or purified form, i.e. substantially pure. This may include being in a composition where it represents at least about 90% active ingredient, more preferably at least about 95%, more preferably at least about 98%. Any such composition may, however, include inert carrier materials or other pharmaceutically and physiologically acceptable excipients, such as those required for correct delivery, release and/or stabilisation of the active agent. As noted below, a composition according to the present invention may include in addition to an modulator compound as disclosed, one or more other molecules of therapeutic use, such as an anti-tumour agent.

Products Obtained by Assays of the Invention

The invention further provides compounds obtained by assay methods of the present invention, and compositions comprising said compounds, such as pharmaceutical compositions wherein the compound is in a mixture with a pharmaceutically acceptable carrier or diluent. Examples of suitable carriers or diluents are given in, for example, "Harrison's Principles of Internal Medicine". The carrier may be liquid, e.g. saline, ethanol, glycerol and mixtures thereof, or solid, e.g. in the form of a tablet, or in a semi-solid form such as a gel formulated as a depot formulation or in a transdermally administrable vehicle, such as a transdermal patch.

The invention further provides a method of treatment which includes administering to a patient an agent which interferes with Mina53 oxygenase activity. Such agents may include inhibitors of Mina53 oxygenase activity.

The therapeutic/prophylactic purpose may be related to the treatment of a condition associated with reduced or suboptimal or increased Mina53 levels or activity, or conditions in which have normal Mina53 levels, but where an modulation in activity such as an increase or decrease in Mina53 oxygenase activity is desirable. For example, Mina53 activity may be modulated in the treatment of proliferative disorders. One such example of a proliferative disorder is cancer. In particular, Mina53 inhibitors may be used in the treatment of colon cancer or oesophageal cancer, such as oesophageal squamous cell carcinoma. Other examples of proliferative disorders are plasma cell proliferative disorders. The plasma cell proliferative disorders may be caused by a viral infection, such as infection by hepatitis C virus or Epstein-Barr virus.

A therapeutically effective amount of an agent is typically administered to a subject in need thereof. A therapeutically effective amount is an amount which ameliorates the symptoms of the condition or lessens the suffering caused to the subject by the condition.

Pharmaceutical Compositions

In various further aspects, the present invention thus provides: a pharmaceutical composition, medicament, drug or other composition for such a purpose, the composition comprising one or more agents, compounds or substances as described herein, including inhibitors of 2-OG dependent oxygenase activity; the use of such a composition in a method of medical treatment; a method comprising administration of such a composition to a patient, e.g. for treatment (which may include preventative treatment) of a medical condition as described above; use of such an agent compound or substance in the manufacture of a composition, medicament or drug for administration for any such purpose, e.g. for treatment of a condition as described herein; and a method of making a pharmaceutical composition comprising admixing such an agent, compound or substance with a pharmaceutically acceptable excipient, vehicle or carrier, and optionally other ingredients.

In one embodiment the method for providing a pharmaceutical composition may typically comprise:

(a) identifying an agent by an assay method of the invention; and (b) formulating the agent thus identified with a pharmaceutically acceptable excipient.

The pharmaceutical compositions of the invention may comprise an agent, polypeptide, polynucleotide, vector or antibody according to the invention and a pharmaceutically acceptable excipient.

The agent may be used as sole active agent or in combination with another such agent or with any other active substance, e.g. for anti-tumour therapy another anti-tumour compound or therapy, such as radiotherapy or chemotherapy.

Whatever the agent used in a method of medical treatment of the present invention, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors.

An agent or composition may be administered alone or in combination with other treatments, either simultaneously or sequentially dependent upon the condition to be treated, e.g. as described above.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. In particular they may include a pharmaceutically acceptable excipient. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Liposomes, particularly cationic liposomes, may be used in carrier formulations. Examples of techniques and protocols mentioned above can be found in Remington's Pharmaceutical Sciences, 16th edition, Osol, A. (ed), 1980.

The substance or composition may be administered in a localised manner to a particular site or may be delivered in a manner in which it targets particular cells or tissues, for example using intra-arterial stent based delivery.

Targeting therapies may be used to deliver the active substance more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

In a further embodiment the invention provides for the use of an agent of the invention in the manufacture of a medicament for the treatment of a condition associated with increased or decreased Mina53 oxygenase levels or activity. The condition may, for example, be cancer.

All the documents cited herein are incorporated herein by reference.

The following Examples illustrate the invention.

EXAMPLES

Example 1

Selection of Mina53 for Analysis as a 2-OG Oxygenase

The Mina53 sequence was detected as a homolog of factor inhibiting hypoxia inducible factor (FIH), a known 2-oxoglutarate dependent oxygenase in a sequence profile analysis employing structural and mechanistic data from 2-OG oxygenases that was carried out (FIG. 1) to look for human 2-OG iron dependent oxygenases. These analyses revealed that Mina53 contains a double-stranded β-helix (DSBH) motif that is characteristic of 2-OG dependent oxygenases. Despite the identification of Mina53 as a protein involved in human cell proliferation and extensive knowledge on 2-OG oxygenase structure, Mina53 has not been identified as a 2-OG dependent oxygenase, since many proteins other than 2-OG dependent oxygenases also contain the DSBH motif. Such proteins include, but are not limited to, the JmjC family some but not all of which are 2-OG dependent oxygenases (Clissold & Ponting (2001) Trends Biochem. Sci. 26, 7-9). The DSBH motif is also characteristic of the functionally diverse cupin superfamily (Dunwell et al. (2004) Phytochemistry 65, 7-17). The human protein pirin (Pang et al. (2004) J. Biol. Chem. 279, 1491-8) and FIH contain the DSBH motif, but only the latter is a 2-OG dependent oxygenase.

Mina53 exhibits the conserved 2-His-1-carboxylate facial triad used to bind Fe(II) and the basic residue (here Lysine) characteristics of the 2-OG iron-dependent oxygenases. Given its role in human cell proliferation, Mina53 was selected for analysis as a 2-OG oxygenase.

Example 2

Cloning of Full Length Mina53

In order to get a working assay system with a recombinant enzyme, it is necessary to express that gene encoding the protein and to purify it in such a way that the protein is correctly folded and functionally active.

The cDNA clone of Mina53 was supplied by the Integrated Molecular Analysis of Gene Expression (IMAGE) Consortium (cDNA clone MAGE:3916148). Mina53 was subcloned directly as a Nde I/Sal I fragment into the pet28a(+) vector from Novagen (a commonly used vector for work with E. coli that expresses the protein with a polyhistidine tag to enable purification through nickel affinity chromatography). The integrity of Mina53 was confirmed by DNA sequencing.

Example 3

Cloning of a C-Terminal Truncated Version of Mina53

A truncated version of Mina53 consisting of amino acids 1 to 301 shown in SEQ ID NO: 2 was subcloned into the pet24a+ vector from Novagen (pet24a+ has no additional residues added to the beginning of the enzyme, unlike pet28a+). The truncation was chosen on the basis of sequence homology with FIH, a known 2-oxoglutarate (2-OG) dependent enzyme. The deleted C-terminal amino acids sequence showed no obvious homology with other 2-OG enzymes, so it was postulated that they could be deleted with no loss of enzyme function.

Example 4

Cloning of a C-Terminal and N-Terminal Truncated Version of Mina53

The Mina53 amino acid sequence was assessed for homology to another protein, yxbC which is expressed in *Bacillus subtilis*. *B. subtilis* can be considered the Gram-positive equivalent of *E. coli*. Therefore it might be expected that a truncated Mina53 sequence bearing homology to a *B. subtilis* protein might express more solubly into *E. coli* than full length Mina53. On this basis a doubly truncated Mina53, residues 40-329 was designed and subcloning into pet28a+ was confirmed through DNA sequencing.

Reference Example 1

Expression of Insoluble Mina53 Using Standard Methodology

Expression trials were carried out using both the full-length and C-terminal truncated forms of Mina53, at 37° C. and 28° C. (using a lower temperature gives slower cell metabolism and therefore more time for the protein to fold properly, thus increasing likelihood of getting active proteins of interest), in the presence of varying amounts of IPTG (a chemical that prevents cells from continuing growth and induces protein production). Following expression, the samples were sonicated into lysis buffer using 50 mmol TRIS buffer at pH7.5 in an effort to obtain soluble protein. This was entirely standard and normal methodology, but gave predominantly or totally insoluble Mina53. The 1-301 and 40-309 truncated versions of Mina53 also gave mainly insoluble protein.

Reference Example 2

Expression of Insoluble Mina53 at Reduced Temperatures

The experiments described in Reference Example 1 were repeated using reduced induction temperatures of 20° C. and 15° C., with the other parameters remaining the same. These conditions also gave predominantly insoluble Mina53.

Example 5

Expression of an Increased Amount of Soluble Mina53 Using Increased Salt and Glycerol Concentrations and Increased pH In an attempt to obtain soluble Mina53, the expression trials were repeated (using induction temperatures of 28° C. and 15° C.) and the cells expressing Mina53 were lysed using lysis buffer having increased salt and glycerol concentrations to disrupt non-covalent interactions which might favour aggregation of Mina53.

Cells expressing the full-length and 1-301 truncated forms of Mina53 were lysed in lysis buffer containing 250 mmol NaCl and glycerol at pH7.9 (normal pH of lysis buffer is pH7.5). An increased amount of soluble protein was observed.

Example 6

Further Optimisation of Lysis Buffer

The expression trials of Example 4 were repeated using (a) a lysis buffer in which the NaCl concentration was increased further, to 500 mmol and (b) a lysis buffer containing 500 mmol NaCl plus 1 mmol of the 2-OG oxygenase inhibitor N-oxalylglycine (NOG) and 1 mmol $FeSO_4$.

The increased salt concentration gave a further improvement in solubility. NOG and $FeSO_4$, however, made little difference.

Example 7

Purification of 1-301 Truncated Mina53

The most soluble sample of Mina53 (1-301) from Example 6(a) was purified using Q-sepharose and then phenyl resource column. The purified Mina53 obtained had 2-OG oxygenase activity.

Example 8

Overexpression and Purification of Full Length Mina53

The Mina53/pet28a(+) construct was transformed into *E. coli* BL21(DE3) and grown at 37° C. in 2TY media containing kanamycin (30 μg·ml⁻¹). When the $OD_{600}$ reached 0.8-1.0, the temperature was reduced to 15° C. and IPTG was added to a final concentration of 0.5 mM. The cells were harvested sixteen hours later by centrifugation at 9000 rpm for 15 min at 4° C.

*E. coli* cell pellets were resuspended in sonication buffer (20 mM Tris pH 7.9, 500 nM NaCl, 10% Glycerol) and broken by sonication. Cell debris was removed by centrifugation at 15000 rpm for 30 min at 4° C. The supernatant was then applied at 4° C. to a 10 ml His-Bind metal-binding chromatography resin (Novagen) following the protocol supplied by the manufacturer (the column was eluted into 5 ml fraction in collection tubes containing 5 μl of 0.5M EDTA 20 mM Tris pH7.9, to chelate any free metal leaching from the column). The sample was then desalted using a PD-10 column (Amersham Biosciences) into 20 mM Tris pH 7.9, 125 mM NaCl, 10% Glycerol. The desalted sample was then applied to a 1 ml MonoQ column (Amersham Pharmacia Biotech) with a linear 20 ml gradient of NaCl, from 0 to 0.5 M, in 20 mM Tris-HCl (pH 7.9).

Example 9

Cloning, Overexpression and Purification of Truncated Mina53 A26-V465/pNIC-Bsa4

A N-terminal truncation of Mina53 A26-V465 cloned into pNIC28-Bsa4 was supplied by the Structural Genomics Consortium Oxford. The Mina53 A26-V465/pNIC-Bsa4 construct was transformed into *E. coli* BL21(DE3) and grown at 37° C. in 2TY media containing kanamycin (30 μg·ml⁻¹). When the $OD_{600}$ reached 0.8-1.0, the temperature was reduced to 15° C. and IPTG was added to a final concentration of 0.5 mM. The cells were harvested sixteen hours later by centrifugation at 9000 rpm for 15 min at 4° C.

The Mina53 A26-V465/pNIC-Bsa4 was purified as per the protocol described for Mina53/pet28a(+). The N-terminal His-tag was cleaved by overnight cleavage at 4° C. with AcTEV protease (Invitrogen, 1 U per mg of Mina53). The polyhistidine tagged AcTEV protease was subsequently removed from the sample via metal chelation chromatography.

Example 10

Assay for 2-OG Oxygenase Activity

Once purified full-length His-Mina53 had been obtained it was tested for 2-OG oxygenase activity. A standard assay for this family of enzymes involves the use of [¹⁴C] labelled 2-OG co-substrate. Upon reaction, the ¹⁴C label is released as 14CO₂ gas (old FIG. 2).

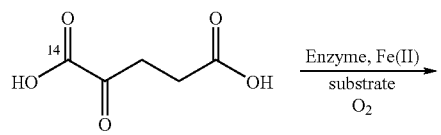

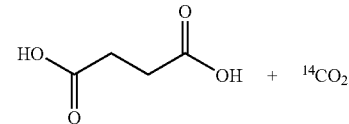

The ¹⁴CO₂ gas is then trapped using a strong base and quantified by liquid scintillation. The level of uncoupled turnover of 2-OG oxygenases can be increased by the use of a reducing agent, e.g. ascorbate. Many other assays for 2-OG oxygenases are well known, e.g. those based on oxygen consumption, succinate production or oxidation of the "prime substrate" (McNeill et al (2005) Anal. Biochem. 336, 125-31; Sabourin & Bieber (1982) J. Biol. Chem. 257, 7460-7; and Cunliffe et al. (1986) Biochem. J. 240, 617-9).

As noted above, many of the enzymes in the family catalyse the decarboxylation of 2-OG in the absence of a suitable prime substrate, albeit at a reduced rate. This activity is sometimes termed as uncoupled turnover. The protocol used for the 2-OG assay decarboxylation is based on the method used to measure [¹⁴CO₂] release by α-ketoisocaproate oxygenase (Sabourin & Bieber (1982) J. Biol. Chem. 257, 7460-7). Standard assay conditions consisted of a total volume of 100 μl, 50 mM Tris-HCl pH 7.5, 4 mM ascorbate, 160 μM 2OG (5% 1-[¹⁴C]), 80 μM $FeSO_4.6H_2O$, 0.48 mg·ml⁻¹ catalase, 10 μM Mina53. Four stocks were made: (a) Mina53 (b) Fe(II) (c) ascorbate and, (d) all other reagents. Assays were started by mixing components (a) to (d). A tube containing 200 μl hyamine hydroxide was added and the vial sealed. The assays were incubated at 37° C. for 20 minutes then quenched with methanol (200 μl). Reaction tubes were then left on ice for 30 mins to collect [¹⁴CO₂] gas, before the hyamine hydroxide was removed and treated with scintillant solution for counting (Beckman, LS6500). Assays were performed in triplicate unless otherwise stated. When potential small molecule inhibitors were added, they were mixed to stock (d) to a final concentration of 1 mM in Tris 50 mM, pH 7.9 buffer. To investigate inhibition of Mina53 by metals other than Fe(II), NiCl2 and ZnCl2 were added separately to the assay mixture to a final concentration of 80 μM.

Using this [¹⁴C] labelled 2-OG assay (16 nm of 2-OG was initially present in the assay mixture), the level of uncoupled turnover for Mina53 was measured under standard catalytic conditions (16 nm of 2-OG was initially present in the assay mixture), in the absence of Fe(II), in the absence of ascorbate and in the presence on N-oxalylglycine (NOG) a ubiquitous inhibitor for the 2-OG dependent non-haem Fe(II) oxygenases[16]. As shown in Table 1, the results show that His-Mina53 is able to decarboxylate 2-OG in the absence of prime substrate under fall catalytic condition. However, the decarboxylation of 2-OG is significantly reduced in the absence of either Fe(II) or ascorbate, and is inhibited by NOG.

TABLE 1

| | Iron, Ascorbate and 2OG dependence of truncated His-Mina53(A26-V465). | | | |
|---|---|---|---|---|
| His-A26-V465 | − | + | + | + |
| Fe(II) | + | + | − | + |
| Ascorbate | + | + | + | − |
| 2OG turnover (nm) | 0.12 ± 0.09 | 6.95 ± 1.72 | 0.51 ± 0.37 | 0.99 ± 0.23 |

The results show that in the presence of ascorbate, Fe(II), 2OG and Mina53(A26-V465), 6.95±1.72 nm of ¹⁴CO₂ gas is released. In the absence of either ascorbate, Fe(II), or Mina53 (A26-V465) the amount of ¹⁴CO₂ gas released is sub-nanomolar.

The inhibition of Mina53 mediated oxidation of 2OG by metals others than Fe(II) was studied. Both Ni and Zn (final assay concentration of 80 μM) were shown to inhibit 2OG turnover, with Zn appearing to be the more potent inhibitor (Table 3).

TABLE 2

Metal inhibition of truncated Mina53(A23-V465)

| | | | | | | |
|---|---|---|---|---|---|---|
| A26-V465 | − | + | + | + | + | + |
| Fe(II) | + | + | − | + | + | + |
| Ascorbate | + | + | + | − | + | + |
| NiCl$_2$ | − | − | − | − | + | − |
| ZnCl$_2$ | − | − | − | − | − | + |
| 2OG turnover (nm) | 0.07 ± 0.02 | 3.84 ± 0.03 | 0.76 ± 0.22 | 0.34 ± 0.16 | 2 ± 0.23 | 0.93 ± 0.17 |

The inhibition of Mina53 mediated oxidation of 2-OG by the following small molecules (FIG. 2) was also studied: N-oxalyl D-phenylalaninie (NOFD) (known to inhibit FIH[17]), prohexadione (a 2-OG analog which inhibits gibberellin biosynthesis in plants[18]), fumarate (known inhibitor of the hypoxia inducible factor hydroxylases), and BB231.

TABLE 3

Selected 2OG analogues structures

| Compound | Structure | Molecular Formula |
|---|---|---|
| NOG | 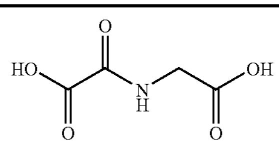 | $C_4H_5NO_5$ |
| Fumarate | 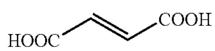 | $C_4H_4O_4$ |
| NOFD | 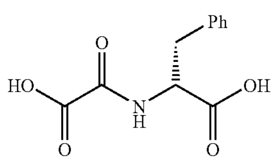 | $C_{11}H_{11}NO_5$ |
| Prohexadione | | $C_{10}H_{12}O_5$ |
| BB231 | | $C_{12}H_9ClN_2O_4$ |

Prohexadione, NOG, and fumarate were shown to inhibit uncoupled 2-OG turnover, while NOFD and BB231 did not significantly reduce it (Table 4).

TABLE 4

Metal and small compound inhibition of truncated Mina53(A26-V465)

| | | | | | |
|---|---|---|---|---|---|
| A26-V465 | + | + | + | + | + |
| Fe(II) | + | + | + | + | + |
| Ascorbate | + | + | + | + | + |
| NOG | + | − | − | − | − |
| NOFD | − | + | − | − | − |
| BB231 | − | − | + | − | − |
| Prohexadione | − | − | − | + | − |
| Fumarate | − | − | − | − | + |
| 2OG turnover (nm) | 0.47 ± 0.12 | 3.86 ± 0.05 | 3.18 ± 0.03 | 0.17 ± 0.12 | 0.58 ± 0.09 |

The invention claimed is:

1. A method for assaying oxygenase activity, the method comprising monitoring oxygenase activity of a polypeptide having greater than about 95% sequence identity with SEQ ID NO: 2.

2. The method of claim 1, wherein the polypeptide is a homologue of Mina53.

3. The method of claim 1, wherein oxygen is used as a co-substrate.

4. The method of claim 1, wherein iron is used as a cofactor.

5. The method of claim 1, wherein a 2-oxoacid is used as a co-substrate.

6. The method of claim 1, wherein 2-oxoglutarate is used as a co-substrate.

7. The method of claim 1, wherein oxygenase activity is monitored in the presence of a reducing agent.

8. The method of claim 7, wherein the reducing agent is ascorbate, or an analogue thereof, a thiol or a phenol.

9. The method of claim 1, wherein oxygenase activity is measured in the presence of a substrate.

10. The method of claim 9, wherein the substrate is a peptide or nucleic acid substrate.

11. A method for assaying oxygenase activity, the method comprising monitoring oxygenase activity of a polypeptide having greater than about 95% sequence identity to a region of SEQ ID NO: 2 between amino acids 128 and 271, 128 and 265 or 161 and 265 and having oxygenase activity.

* * * * *